(12) United States Patent
Aparicio et al.

(10) Patent No.: US 11,147,746 B2
(45) Date of Patent: Oct. 19, 2021

(54) HYDROPHOBIC DENTAL SURFACES

(71) Applicant: Regents of the University of Minnesota, Minneapolis, MN (US)

(72) Inventors: Conrado Aparicio, Minneapolis, MN (US); Alex Fok, Minneapolis, MN (US); Dina G. Moussa, Minneapolis, MN (US); Brian Holmes, Minneapolis, MN (US); William H. Douglas, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 18 days.

(21) Appl. No.: 15/629,430

(22) Filed: Jun. 21, 2017

(65) Prior Publication Data

US 2017/0367933 A1 Dec. 28, 2017

Related U.S. Application Data

(60) Provisional application No. 62/354,519, filed on Jun. 24, 2016.

(51) Int. Cl.
*A61C 5/00* (2017.01)
*A61K 6/20* (2020.01)
(Continued)

(52) U.S. Cl.
CPC .............. *A61K 6/20* (2020.01); *A61C 5/00* (2013.01); *A61K 6/69* (2020.01); *A61K 6/884* (2020.01)

(58) Field of Classification Search
CPC ...... A61C 5/00; A61K 6/0017; A61K 6/0067; A61K 6/08
(Continued)

(56) References Cited

U.S. PATENT DOCUMENTS 5,607,663 A * 3/1997 Rozzi .................. A61K 6/0017
424/49
5,866,630 A * 2/1999 Mitra .................. A61K 6/0017
424/49
(Continued)

FOREIGN PATENT DOCUMENTS

EP 2674145 A1 12/2013

OTHER PUBLICATIONS

Chen, Xi, et al., Antimicrobial GL13K Peptide Coatings Killed and Ruptured the Wall of *Streptococcus gordonii* and Prevented Formation and Growth of Biofilms, Nov. 5, 2014, PLOS one, vol. 9 Issue 11, pp. 1-8 (Year: 2014).*

(Continued)

*Primary Examiner* — Matthew M Nelson
(74) *Attorney, Agent, or Firm* — Shumaker & Sieffert, P.A.

(57) ABSTRACT

An example article may include a dental surface, a hydrophobic coating on the dental surface, and a restorative layer on the hydrophobic coating. An example technique may include applying, on a dental surface, a hydrophobic coating comprising an amphiphilic agent. The hydrophobic coating may provide a water contact angle of greater than or equal to about 50° on the dental surface. The example technique may include applying a restorative layer to the hydrophobic coating. An example kit may include a dental restorative composition and a hydrophobic coating composition. The hydrophobic coating composition may include an amphiphilic agent. The hydrophobic coating composition may be configured to provide a water contact angle of greater than or equal to about 50° on a dental surface.

22 Claims, 17 Drawing Sheets
Specification includes a Sequence Listing.

(51) Int. Cl.
*A61K 6/69* (2020.01)
*A61K 6/884* (2020.01)

(58) Field of Classification Search
USPC .......................................................... 433/73
See application file for complete search history.

(56) References Cited

U.S. PATENT DOCUMENTS

| | | | | |
|---|---|---|---|---|
| 6,387,982 | B1* | 5/2002 | Blackwell | C08G 18/673 523/118 |
| 6,407,148 | B1* | 6/2002 | Krejci | A61K 6/0017 106/35 |
| 2001/0012509 | A1* | 8/2001 | Mitra | A61K 6/0017 424/49 |
| 2006/0078510 | A1* | 4/2006 | Takei | A61K 6/0017 424/49 |
| 2006/0270751 | A1* | 11/2006 | Thalacker | A61K 6/0061 523/116 |
| 2010/0216907 | A1* | 8/2010 | Matsushige | A61K 6/0017 522/154 |
| 2013/0217800 | A1* | 8/2013 | Suh | C08F 2/48 522/30 |
| 2017/0196778 | A1* | 7/2017 | Nojiri | A61K 6/00 |
| 2018/0200153 | A1* | 7/2018 | Hill | A61K 6/0005 |
| 2018/0200164 | A1* | 7/2018 | Latta | A61Q 13/00 |

OTHER PUBLICATIONS

Department of Health and Human Services Part 1. Overview Information, accessed from httos://grants.nih.gov/grants/guide/rfa-files/RFA-DE-16-007.html posted on Jun. 11, 2015, 15 pp.

Spencer et al., "Adhesive/Dentin Interface: The Weak Link in the Composite Restoration," Ann Biomed Eng., NIH Public Access, Jun. 1, 2010, 24 pp.

Su et al., "Antibacterial effect and bond strength of a modified dental adhesive containing the peptide nisin," Elsevier, Oct. 6, 2017, 6 pp.

Tian et al., "Paucity of Nanolayering in Resin-Dentin Interfaces of MDP-based Adhesives," Journal of Dental Research, Mar. 21, 2016, 8 pp.

Xie et al., "Novel dental adhesive with triple benefits of calcium phosphate recharge, protein-repellent and antibacterial functions," Elsevier, Mar. 9, 2017, 11 pp.

Ye et al., Engineered Peptide Repairs Defective Adhesive-Dentin Interface, Macromol Mater Eng. HHS Public Access, Oct. 20, 2017, 12 pp.

Yuca et al., "Chimeric biomolecules: biomolecular recognition-based self-organization at the bio-material interfaces," Chapter 12 of Material-Tissue Interfacial Phenomena, published Oct. 11, 2016, 285-324 pp.

Zhang et al., "On the Durability of Resin-Dentin Bonds: Identifying the Weakest Links," Dent Mater, HHS Public Access, Sep. 31, 2015, 23 pp.

Cao et al., "Fabrication of superhydrophobic coating for preventing microleakage in a dental composite restoration," Materials Science and Engineering, Apr. 14, 2017, 8 pp.

* cited by examiner

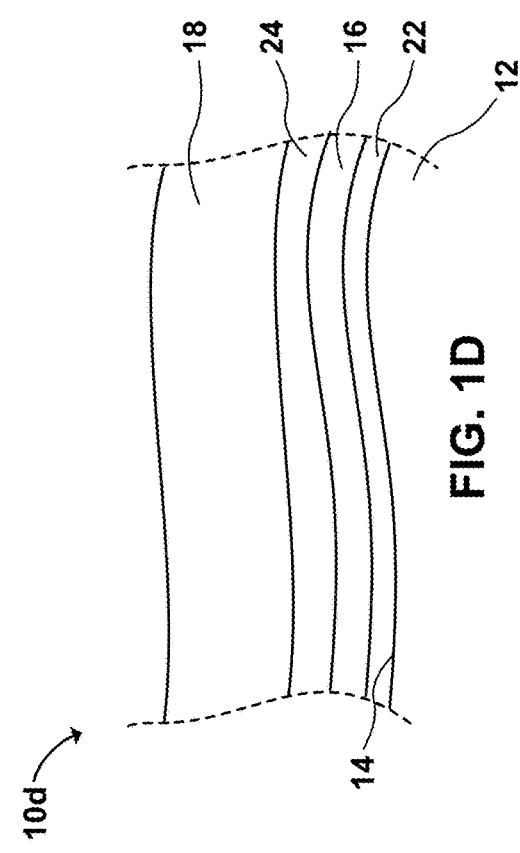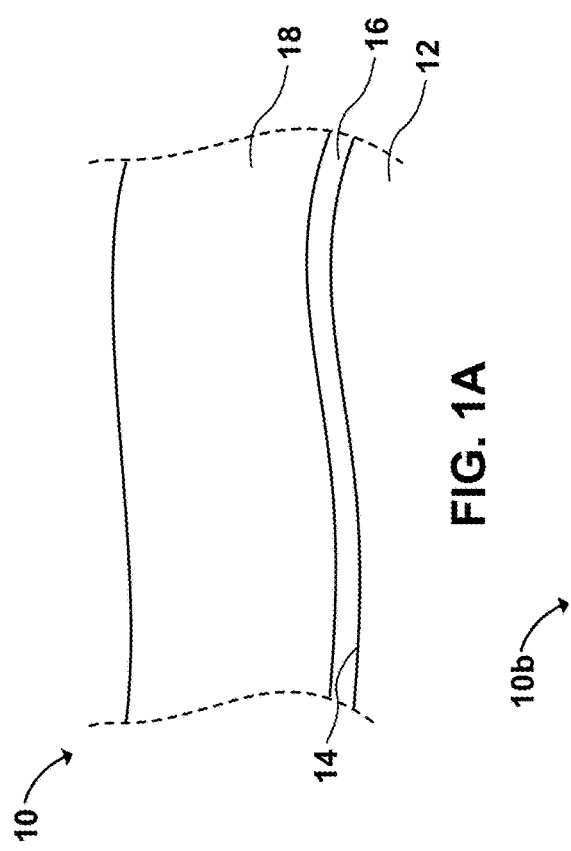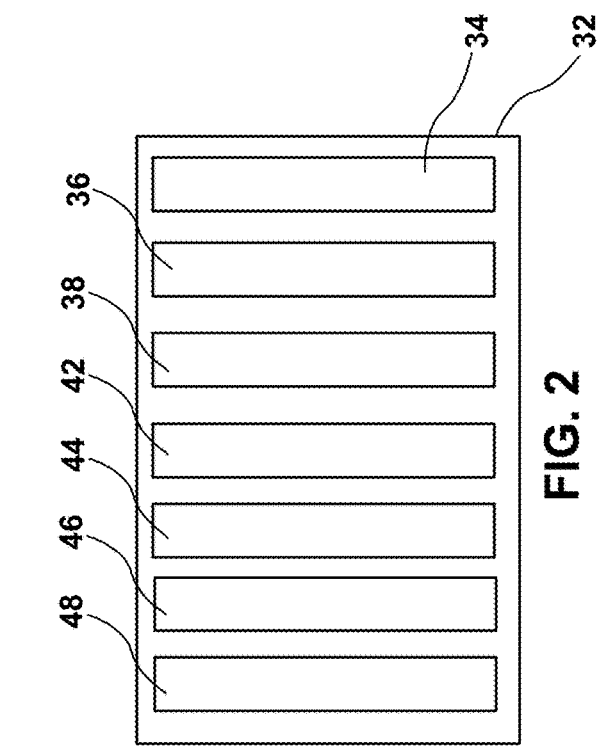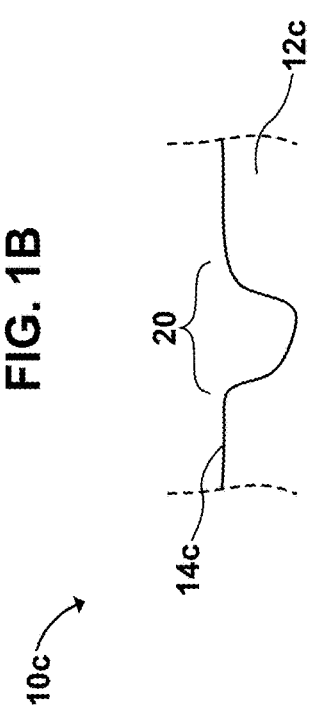

HYDROPHOBIC DENTAL SURFACES

This application claims the benefit of U.S. Provisional Patent Application No. 62/354,519 filed Jun. 24, 2016, the entire content being incorporated herein by reference.

REFERENCE TO SEQUENCE LISTING, TABLE OR COMPUTER PROGRAM

The Sequence Listing submitted herewith in a computer readable form (CRF) by electronic submission via EFS-Web as file name Sequence_Listing_ST25-06.15.2017.txt is herein incorporated by reference. The electronic copy of the Sequence Listing was created on Jun. 15, 2017, with a file size of 685 bytes.

TECHNICAL FIELD

This disclosure relates to dental surfaces.

BACKGROUND

Damaged or diseased dental surfaces, for example, teeth having caries, may be restored with aesthetic filling materials. Teeth may also be restored for cosmetic purposes. Dental practitioners may cut predetermined regions of teeth to expose a cavity with walls of enamel and/or dentin and then use restorative materials, such as dental resin-based adhesives systems and composites to restore teeth.

SUMMARY

In some examples, the disclosure describes an example technique including applying, on a dental surface, a hydrophobic coating comprising an amphiphilic agent to provide a water contact angle of greater than or equal to about 50° on the dental surface. The example technique may include applying a restorative layer to the hydrophobic coating.

In some examples, the disclosure describes an example article including a dental surface, a hydrophobic coating on the dental surface, and a restorative layer on the hydrophobic coating. The hydrophobic coating may provide a water contact angle of greater than or equal to about 50° on the dental surface.

In some examples, the disclosure describes an example kit including a dental restorative composition and a hydrophobic coating composition. The hydrophobic coating composition may include an amphiphilic agent. The hydrophobic coating composition may be configured to provide a water contact angle of greater than or equal to about 50° on a dental surface.

The details of one or more examples are set forth in the accompanying drawings and the description below. Other features, objects, and advantages will be apparent from the description and drawings, and from the claims.

BRIEF DESCRIPTION OF SEQUENCE LISTINGS

SEQ ID NO:1 is a peptide known as GL13K.
SEQ ID NO:2 is a peptide known as peptide 1018.

BRIEF DESCRIPTION OF DRAWINGS

FIG. 1A is a conceptual and schematic diagram illustrating an example article including a hydrophobic coating on a dental surface and a restorative layer.

FIG. 1B is a conceptual and schematic diagram illustrating an example article including an etched dental surface.

FIG. 1C is a conceptual and schematic diagram illustrating an example article including a dental surface including a cavity.

FIG. 1D is a conceptual and schematic diagram illustrating an example article including a hydrophobic coating on a dental surface and a restorative layer.

FIG. 2 is a conceptual and schematic diagram illustrating an example kit including a hydrophobic coating composition and a dental restorative composition.

DETAILED DESCRIPTION

Figure 1E:
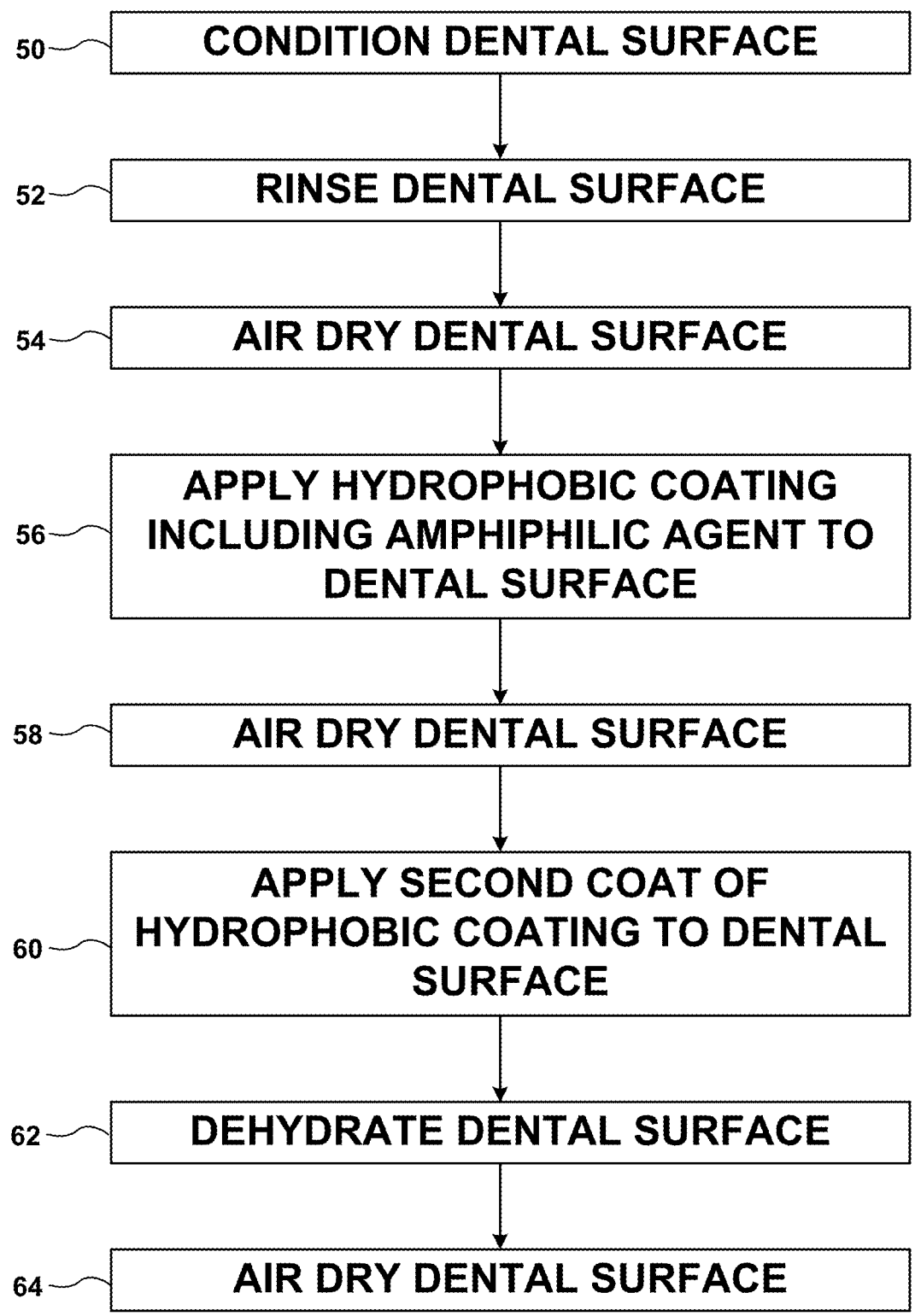
FIG. 1E is a flow diagram of an example technique for applying a hydrophobic coating on a dental surface.

According to the disclosure, hydrophobic surfaces include surfaces that exhibit a water contact angle of greater than or equal to about 50°. Hydrophobic surfaces according to the disclosure may also include highly hydrophobic surfaces or super-hydrophobic surfaces, or surfaces that exhibit a relatively high water contact angle, for example, a water contact angle of greater than or equal to about 100°. In some examples, a surface may be referred to as being hydrophobic after a treatment or a process if the water contact angle exhibited by the surface increases due to the treatment or process.

In the course of dental restoration with dental resin-based composites or other esthetic dental restorative materials, walls of enamel and/or dentin may be etched. The etching produces rough enamel surfaces and microporous demineralized dentin surfaces containing exposed collagen with water. Thus, without being bound by theory, etching demineralizes dentin and exposes a matrix of collagen ready to be infiltrated by the bonding agent. Etched tissues may be wet and/or infiltrated by bonding resin-based agents (for example, primer and adhesive). Bonding agents may be hydrophilic to strongly interact with the naturally hydrophilic dentin. For example, hydrophilic agents sufficiently interact with the tooth tissues for providing good retention. Bonding agents/adhesives may be applied with or without the prior application of a primer. The use of self-etching bonding agents/adhesives may avoid the need for a separate etching step. Bonding agents may include some amphiphilic components to facilitate bonding with the esthetic restorative material. Restorative materials may typically include a hydrophobic resin composite.

However, the hydrophilic bonding agent may act as a semi-permeable membrane that allows water exchange at the dentin/restoration/oral cavity interface, which may facilitate its degradation. Tooth-restoration interfaces may thus be prone to biofilm accumulation and bio-degradation, for example, being susceptible to water-, acid-, enzyme-, and bacteria-mediated degradation.

Example techniques, articles, and kits according to the disclosure may prevent water-, acid-, enzyme-, and bacteria-mediated degradation. For example, example techniques may include coating dental surfaces, for example, etched tooth tissues, with amphiphilic molecules to form hydrophobic tissue/air, or tissue/dental material interfaces and super-lipophilic tissue/water interfaces. Amphiphilic molecules may self-organize on tissue surfaces to produce stable hydrophobic interfaces with restorative materials. Coatings may include both synthetic (anionic and ionic surfactants, such as sodium dodecyl sulfate (anionic), benzalkonium chloride (cationic), cocamidopropyl betaine (zwitterionic) and 1-octanol (long chain alcohol, non-ionic), amphiphilic block co-polymers, recombinant biopolymers/recombinamers (for example, elastin-like and silk-like recombinant polymers) and biological (amphiphilic peptides and peptidomimetics, proteins, and carbohydrates, phopspholipids, fatty acids, etc.) amphiphilic molecules can be used. For example, example coatings may include an amphiphilic and antimicrobial peptide molecule, GL13K, a molecule represented by the amino acid sequence of SEQ ID NO: 1.

```
                                            (SEQ ID NO: 1)
Gly Lys Ile Ile Lys Leu Lys Ala Ser Leu Lys Leu Leu
```

In some examples, example coatings may include peptide 1018 (also known as innate defense regulator 1018, or IDR-1018), a molecule represented by the amino acid sequence of SEQ ID NO:2.

```
                                            (SEQ ID NO: 2)
Val Arg Leu Ile Val Ala Val Arg Ile Trp Arg Arg
```

In some examples, one or more peptides according to the disclosure are carboxy-amidated at their respective carboxyl termini. In some examples, peptides according to the disclosure include peptides having the amino acid sequence of SEQ ID NOS: 1-2, and analogs, derivatives, enantiomers, reversed sequences, amidated, or unamidated, variants. Providing amphiphilic molecules in the coating may protect both dental tissues and esthetic restorative dental materials from water-meditated (hydrolytic, acidic, enzymatic) and bacterial degradation. Water, acids, enzymes and bacteria are some agents that may degrade dental restorations, for example, at tissue/bonding agent and bonding agent/dental composite interfaces that may result in premature failure of the restoration. In some examples, example coatings may include amphiphilic molecules that are antimicrobial, for example, molecules such as GL13K.

Coating tissue surfaces with amphiphilic molecules may result in hydrophobic surfaces that may be used with bonding agents having relatively greater hydrophobicity compared to untreated tissue surfaces, for example, leading to better integration with the resin composites. Hydrophobic or tissue surfaces may also be bonded directly to hydrophobic dental composites, which may reduce the number of steps of the restorative procedure, for example, by avoiding the need for applying bonding agents. Thus, according to example techniques, compositions and kits of the disclosure, one or more of the following may be provided: a hydrophobic tooth-restoration interface that may improve the performance of esthetic dental restorations, for example, by preventing degradation of the restoration and tissue interfaces, an antimicrobial tooth-restoration interface that may improve the performance of esthetic dental restorations, synthetic and/or biological amphiphilic molecules that may provide super-hydrophobic tissue surfaces, hydrophobic adhesives that may be used to bond esthetic restorations to hydrophobic tissue surfaces, and direct bonding of esthetic restorative composites to the hydrophobic tissue surfaces.

FIG. 1A is a conceptual and schematic diagram illustrating an example article including a hydrophobic coating on a dental surface and a restorative layer. Article 10 includes a dental substrate 12 having a dental surface 14, a hydrophobic coating 16 on dental surface 14, and a restorative layer 18 adjacent the dental surface 14. Dental substrate 12 may include any suitable dental substrate, for example, a region of a tooth or a dental prosthetic. In some examples, dental surface 14 of dental substrate 12 may be etched. For example, FIG. 1B is a conceptual and schematic diagram illustrating example article 10b including an etched dental surface 14b. The etching on dental surface 14b may or may not be visible to the naked eye. In some examples, instead of etching, or in addition to etching, one or both of dehydration or deproteinization of dental surface 14 may be performed. One or more of etching, dehydration, and deproteinization may render dental surface 14 more susceptible to one or both of the hydrophobic coating 16 and restorative layer 18. Referring to FIG. 1A, in some examples, dental surface 14 may include one or more of dentin, enamel, or a dental prosthetic. For example, dental surface 14 may include dentin or enamel tissue. In some examples, dental surface 14 may include a cavity. For example, FIG. 1C is a conceptual and schematic diagram illustrating an example article 10c including a dental substrate 12c having a dental surface 14c including a cavity 20. In some examples, cavity 20 may include a cavity drilled in dental substrate 12c in course of dental or cosmetic treatment or restoration.

Hydrophobic coating 16 may be disposed on dental substrate 12, for example, adjacent dental surface 14. In some examples, dental surfaces 14, 14b, or 14c may be provided with hydrophobic coating 16. Hydrophobic coating 16 may include a hydrophobic coating composition, and may be provided on dental surface 14 by applying the hydrophobic coating composition to dental surface 14. Hydrophobic coating 16 may include an amphiphilic agent. The hydrophobic coating may provide a water contact angle to the dental surface that may be greater than the water contact angle of an uncoated dental surface. For example, an uncoated dental surface 14 or uncoated etched dental surface 14b may exhibit a relatively low water contact angle, for example, of less than 70°, or less than 60°, or less than 50°. In contrast, dental surface 14 coated with hydrophobic coating 16 may exhibit a relatively high water contact angle, for example, a water contact angle of greater than or equal to about 50°, greater than or equal to about 70°, or greater than or equal to about 100°, or greater than or equal to about 120°.

The water contact angle (WCA) may be measured using the sessile drop method with deionized water as probe liquid. The sessile drop is the most common method for optical measurement of the contact angle using drop shape analysis. Measurement of the contact angle of a sessile drop that lies on the surface of a solid may be made with a contact angle goniometer, which allows measuring the contact angle visually by capturing the profile of a pure liquid on a solid substrate. The angle formed between the liquid-solid interface and the liquid-vapor interface is determined to be the water contact angle. A droplet is deposited by a syringe which is positioned above the sample surface, and a high-resolution camera may be used to capture the image from the profile or side view. The image may be analyzed using image analysis software. The measurement may be referred to as a static contact angle measurement. The change in WCA, or $\Delta$WCA, is the difference between the average water contact angles after predetermined intervals of time, for example, 1 s and 21 s of drop contact with the tested surface, or the difference between the initial and the final water contact angles.

Water contact angles described according to the disclosure are with reference to the sessile drop technique, using a drop volume or 2-5 µL, for example, 3 µL. Similar or different values of WCA and $\Delta$WCA for the same tested surfaces may be obtained using other methods to determine wettability of surfaces, such as the Wilhelmy method, or when using different drop volumes. In some examples, one or more of these or other techniques may be used to determine the WCA or $\Delta$WCA.

Hydrophobic coating 16 may include one or more suitable amphiphilic agents. For example, amphiphilic agents may include amphiphilic molecules having both hydrophobic and hydrophilic regions, or zones, for example, a hydrophobic head and a hydrophilic tail or a hydrophobic tail and a hydrophilic head. Amphiphilic agents may assist in the formation of hydrophobic tissue/air or tissue/dental material interfaces and lipophilic tissue-water interfaces. Amphiphilic agents such as amphiphilic molecules may organize on tissue surfaces to offer stable hydrophobic interfaces with restorative materials. In some examples, amphiphilic agents may include synthetic (anionic and ionic) surfactants, such as sodium dodecyl sulfate (anionic), benzalkonium chloride (cationic), cocamidopropyl betaine (zwitterionic) and 1-octanol (long chain alcohol, non-ionic), polianionic and polyionic molecules, amphiphilic block co-polymers, recombinant biopolymers/recombinamers (for example, elastin-like and silk-like recombinant polymers) and biological (amphiphilic peptides and peptidomimetics, proteins, phopspholipids, fatty acids, and carbohydrates) amphiphilic molecules, and combinations thereof. For example, hydrophobic coating 16 may include GL13K peptide. In some examples, hydrophobic coating 16 may consist of GL13K peptide, 1018 peptide, D-enantiomeric GL13K peptide, D-enantiomeric 1018 peptide, randomized aminoacid versions of the previous molecules, reversed aminoacid versions of the previous molecules, one or both of water and a buffer solution, and combinations thereof. For example, hydrophobic coating 16 may consist of GL13K peptide and water, or GL13K peptide and a buffer solution, or GL13K peptide, water, and buffer solution. In some examples, hydrophobic coating 16 may consist of GL13K peptide. In some examples, GL13K molecules may orient in hydrophobic coating 16 such that their hydrophilic ends are oriented towards dental surface 14 while their hydrophobic ends are oriented away from dental surface 14. For example, hydrophobic coating 16 may include only GL13K molecules, and exclude other molecules. In some examples, the amphiphilic agent may be an antimicrobial agent. For example, the amphiphilic agent may act as an antimicrobial agent. An antimicrobial agent is an agent that may have a bacteriostatic, bactericidal, fungicidal, biocidal, sterilizing effect or otherwise reduce microbial activity or population, or prevent the growth of microbial activity or populations. For example, GL13K may act as both an amphiphilic agent and an antimicrobial agent in hydrophobic coating 16.

Restorative layer 18 may be applied to dental substrate 12. For example, restorative layer 18 may be applied on dental surface 14 coated with hydrophobic coating 16. In some examples, hydrophobic coating 16 may substantially cover a major region of dental surface 14 so that hydrophobic coating 16 is between dental restorative layer 18 and dental surface 14 across dental surface 14. In some examples, hydrophobic coating 16 may have a relatively uniform thickness separating restorative layer 18 from dental surface 14. In some examples, hydrophobic coating 16 may include voids or gaps so that restorative layer 18 may directly contact dental surface 14 at some regions. In some examples, restorative layer 18 may include a dental restorative composition. For example, restorative layer 18 may include a composite dental resin. In some examples, the composite dental resin may be curable by UV light. In some examples, the composite dental resin may be self-cured, for example, by mixing two components. In some examples, the restorative layer 18 may include a hydrophobic material, or may exhibit hydrophobicity. In some examples, restorative layer 18 may be part of a larger restorative region, for example, a bulk restoration region. In some examples, restorative layer 18 may include a cured or set dental restorative material. In some examples, dental substrate 12 or dental surface 14 may include dental restorative material, for example, from a previous restoration. Thus, in some examples, restorative layer 18 may be applied on a region of dental surface 14 that includes a cured or set dental restorative material.

While in the examples described with reference to FIG. 1A, hydrophobic layer 16 is disposed adjacent or between restorative layer 18 and dental surface 14, in some examples, hydrophobic layer 16 may be disposed at any suitable position relative to dental surface 14. For example, hydrophobic coating 16 may directly contact one or both of dental surface 14 and restorative layer 18. In some examples, hydrophobic coating 16 may be separate from one or both of dental surface 14 and restorative layer 18 by other layers. For example, FIG. 1D is a conceptual and schematic diagram illustrating an example article 10d including hydrophobic coating 16 on dental surface 14 and restorative layer 18, further including a primer layer 22 and an adhesive layer 24. In some examples, article 10d may include one or both of primer layer 22 and adhesive layer 24. For example, primer layer 22 may allow for improved bonding or uniform application of adhesive layer 24 to dental surface 14. Primer layer 22 may penetrate pores, voids, or exposed regions of dental surface 14, for example, regions exposed by one or more of etchant, dehydration, or deproteinization. While in the example shown in FIG. 1D, primer layer 22 is between hydrophobic coating 16 and dental surface 14, in other examples, hydrophobic coating may be disposed between primer layer 22 and dental surface 14. In some examples, primer layer 22 may be hydrophilic. In some examples, providing hydrophobicity to dental surface 14 may allow the use of primer layer 22 that is hydrophobic instead of hydrophilic. In some examples, adhesive layer 24 may be applied without primer layer 22. Adhesive layer 24 may promote the adhesion or retention of restorative layer 18 on dental surface 14. Adhesive layer 24 may include any suitable adhesive for bonding restorative layer 18 to dental surface 14. In some examples, adhesive layer 24 may include an adhesive composition that includes an etchant or an adhesive that is self-etching. In some examples, providing hydrophobicity to dental surface 14 may allow the use of adhesive layer 24 that is hydrophobic.

FIG. 1E is a flow diagram of an example technique for applying a hydrophobic coating on a dental surface. Example articles described above with reference to FIGS. 1A-1D may be prepared using example techniques described with reference to FIG. 1E. While some example techniques are described with reference to the example article of FIG. 1D, the example techniques described below could be used to prepare other example articles according to the disclosure. In some examples, the example technique of FIG. 1E includes conditioning dental surface 14 (50). The conditioning may include preparing dental surface 14 for applying hydrophobic coating 16, for example, one or both of etching or deproteinizing dental surface 14. Dental surface 14 may be cleaned, for example, by rinsing dental surface 14 (52). The rinsing (52) may include rinsing or washing dental surface 14 with water or any suitable dental cleaning agent. In some examples, dental surface 14 may optionally be dried after one or both of conditioning (50) or rinsing (52), for example, by air drying dental surface 14 (54).

After one or more of optionally conditioning (50), rinsing (52) or air drying (54), the example technique of FIG. 1E may include applying, on dental surface 14, hydrophobic coating 16 comprising an amphiphilic agent (56). Hydrophobic coating 16 may provide a water contact angle of greater than or equal to about 50° on dental surface 14. For example, hydrophobic coating 16 may be applied by applying a hydrophobic coating composition to dental surface 14, for example by extrusion from a container or by transferring a volume of the hydrophobic coating composition from a container to a dental implement and from the dental implement to dental surface 14. The example technique may include applying restorative layer 18 to hydrophobic coating 16 or dental surface 14. For example, restorative layer 18 may be applied by applying a dental restorative composition to dental surface 14 or hydrophobic coating 16, for example by extrusion from a container or by transferring a volume of the dental restorative composition from a container to a dental implement and from the dental implement to dental surface 14 or hydrophobic coating 16. In some examples, after applying hydrophobic coating 16 (56), the example technique may include one or both of air drying dental surface 14 (58) and applying a second coat of hydrophobic coating 16 (60) to dental surface 14. The second coat may include the same or similar hydrophobic composition as the first coat, or may have a different hydrophobic composition.

In some examples, the example technique may include, before the applying of one or both of hydrophobic coating 16 or restorative layer 18 (56), conditioning dental surface 14 by applying an etchant composition on dental surface 14 to etch dental surface 14 (50). The etchant composition may include any suitable etching agent or abrasive. Applying the etchant during conditioning (50) may one or both of roughen dental surface 14 or demineralize dentin or enamel to produce an infiltrable surface.

In some examples, the example technique may include dehydration of dental surface 14 (62). For example, a dehydrating composition may be applied to dental surface 14 to dehydrate dental surface 14. In some examples, the dehydrating composition may include volatiles or other dehydrating agents, for example, alcohols, acetones, ketones, or combinations thereof. In some examples, the example technique may include applying a deproteinization agent to dental surface 14. For example, the deproteinization agent may include one or more of bleach, sodium hypochlorite, or enzymes such as proteolytic enzymes. The dehydrating (62) may result in partial, substantial, or substantially complete dehydration (removal of water or moisture) of dental surface 14. In some examples, the dehydrating (62) may be performed by using sequential treatment with increasing concentration of dehydrating agent, for example, with 50%, 70%, 80%, 95%, and 100% by volume of the dehydrating agent, for example, alcohol.

While etching, dehydration, and deproteinization have been described, in some examples, the example technique may include multiple steps of conditioning (50), dehydration (62), or drying, for example, before or after the applying of hydrophobic coating 16 or restorative layer 18. In some examples, none of etching, dehydration, and deproteinization may be performed, and the example technique may substantially include only applying of one or both of hydrophobic coating 16 or restorative layer 18. In some examples, one or more of the applying hydrophobic coating, applying restorative layer 18, etching, dehydrating, and deproteinization may be performed by spraying, dripping, brushing, rinsing, or flushing respective hydrophobic, restorative, etchant, dehydration, and deproteinization compositions on dental surface 14. In some examples, the example technique may include one or more of cutting dental surface 14 to expose a cavity, applying an etchant composition on dental surface 14, applying primer layer 22 on dental surface 14, and applying adhesive layer 24 on dental surface 14. In some examples, restorative layer 18 may be cured or set, for example, by exposure to UV light, before, during, or after applying one or more layers on dental surface 14.

The example techniques described with reference to FIG. 1E may be performed by dental practitioners using example dental kits described below to result in example articles, for example, example articles described with reference to FIGS. 1A-1D. However, the example techniques may be performed by dental practitioners using other kits according to the disclosure, or by assembling appropriate components described above.

FIG. 2 is a conceptual and schematic diagram illustrating an example kit 30 including a hydrophobic coating composition 34 and a dental restorative composition 36. In some examples, example kit 30 may further include one or more of an etchant composition 38, a primer composition 42, an adhesive composition 44, a dehydrating composition 46, and a deproteinization composition 48. In some examples, example kit 30 may include a kit body 32. For example, kit body 32 may be a flexible, rigid, or semi-rigid container configured to hold one or more flexible, rigid, or semi-rigid containers comprising one or more of dental compositions 34, 36, 38, 42, 44, 46, and 48. In some examples, kit container 32 may include chambers in which one or more of dental compositions 34, 36, 38, 42, 44, 46, and 48 may be disposed. In some examples, dental compositions may be disposed in respective sub-containers housed in kit container 32. In some examples, one or more of example kit 30, kit container 32, or respective sub-containers may be sterilized or otherwise in a sterile environment. In some examples, one or more of kit container 32, and sub-containers containing dental compositions 34, 36, 38, 42, 44, 46, and 48 may include one or more of metal, plastic, rubber, glass, fabric, or other suitable material. In some examples, one or more of sub-containers containing dental compositions 34, 36, 38, 42, 44, 46, and 48 may include a spray container, for example, a pressurized or non-pressurized spray container.

In some examples, example kit 30 may include one or more dental implements (not shown). For example, the dental implements may include one or more shared or dedicated applicators for applying respective compositions, for example, a syringe, a spatula, a carver, a sprayer, or any other soft, semi-rigid, or rigid applicators or implements. In some examples, the dental implements may be sterilized or maintained in sterile environments, for example, shared or dedicated sterile envelopes, pouches, or other containers.

Thus, in performing restorative dental techniques according to example techniques, a dental practitioner may use one or more components of example kit 30 to perform one or more steps of example techniques, for example, to arrive at one or more example articles. Thus, example articles, techniques and kits according to the disclosure may be used for dental restoration.

The present disclosure will be illustrated by the following non-limiting examples.

EXAMPLES

Example 1

Dental surfaces were treated with GL13K, D-GL13K, or 1018 peptides to obtain hydrophobic surfaces. The wettability of coated etched dentin with these peptides was evaluated in different conditions, for example, single or double GL13K coatings, rinsing with water or alcohol after coating, after deproteinization, with blow drying, alcohol drying, combinations of the two, or progressive alcohol drying after dentin etching, and using the same buffer solutions with or without peptides. Dynamic water contact angles (WCA) of water drops placed on the treated dentin surfaces were measured.

A drop of 3 µL of deionized water was dispensed using a contact angle meter (DCM-E1, Kyowa, Japan) on top of the dentin surfaces with and without treatments. Images of the drop were automatically taken with the camera of the contact angle meter every second for 21 s; i.e., until the shape of the drop on the surface was stable for all surfaces analyzed. The shape of the profile of the drop on the surface was then automatically identified by the equipment's software (Famas, Kyowa, Japan) and the contact angle between the liquid-solid interface and the liquid-vapor interface was determined. The reported WCA are average values at the end of the test; i.e., after 21 s the drop was in contact with the tested surface for at least 3 different drops in three different surfaces for each dentin treatment. ΔWCA is the difference between the average water contact angles after 1 s and 21 s of drop contact with the tested surface; i.e., the difference between the initial and the final water contact angles.

TABLE 1 summarizes some results. The WCA of etched dentin was 20°, expressing dynamic changes over 20 seconds (ΔWCA) of around 25°, which demonstrated its known hydrophilic character and water penetration over time in the open tubular structure of etched dentin. Based on the GL13K peptide's strong amphiphilic properties, the hydrophilic etched dentin was expected to attract the hydrophilic side of GL13K, leaving the hydrophobic side of the peptide exposed at the interface. When a single coating of GL13K was applied to etched dentin, followed by an alcohol rinse or water rinse and blow drying, the WCA increased to 55° or 70°, respectively; i.e., GL13K-coated dentin showed hydrophobic properties. Applying two GL13K coating treatments and rinsing the coated samples with alcohol further increased the WCA to 100°. Similar results were obtained with samples of both enamel-lined and pulp-lined dentin;

therefore, the size of the dentinal tubules did not affect the hydrophobic character of the coated dentin. In all cases where GL13K coatings were applied, the variation of water contact angle over time was significantly reduced with respect to the etched dentin. This indicates that the GL13K hydrophobic coatings hindered water penetration through the open tubular structure of etched dentin. The collagen fibres in the demineralized dentin were determined to have collapsed upon alcohol rinsing.

To increase further the amount of GL13K molecules retained on etched dentin and, thus, the hydrophobicity, progressive dehydration of dentin using increasing ethanol concentrations was performed, which suspended the demineralized collagen matrix in its dehydrated but fully extended state. Eliminating the in-between water nano-channels resulted in full expansion of the interfibrillar spaces, which was expected to increase the dried collagen surface area available to interact with the peptides.

Figure 3:
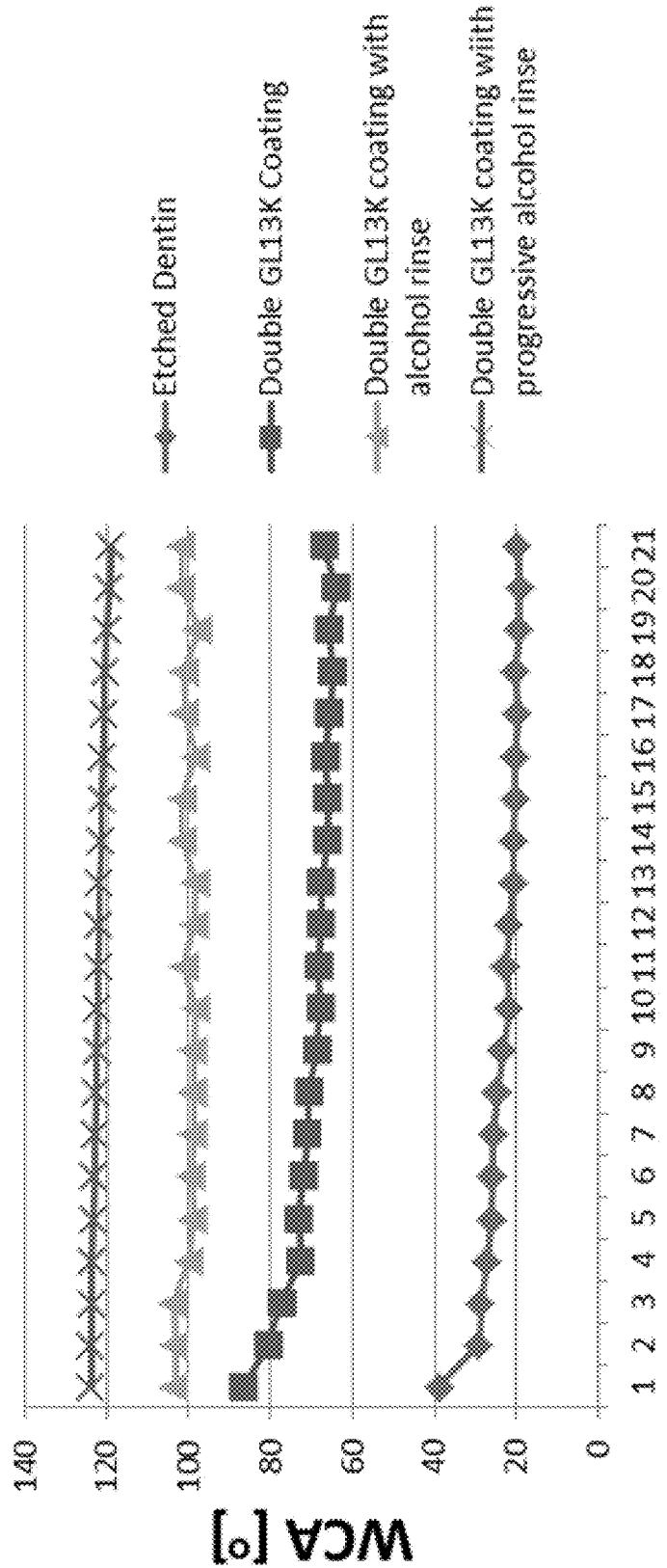
FIG. 3 is a chart presenting water contact angle as a function of time for untreated dental surfaces and dental surfaces treated with GL13K.
Figure 4A:
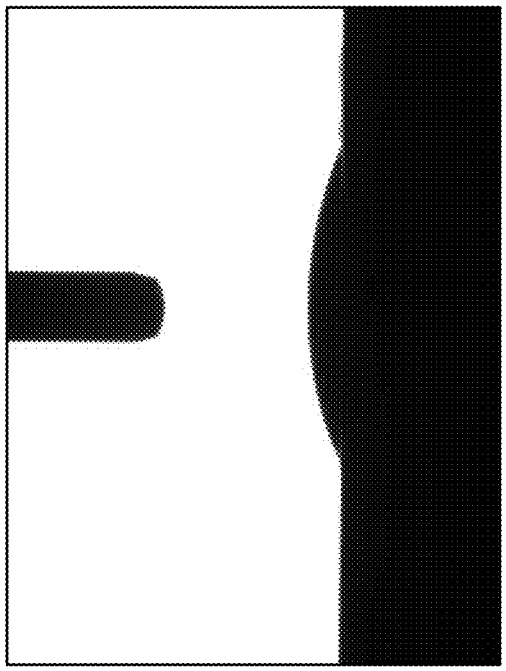
FIG. 4A is a photograph showing a water drop disposed on an untreated dentin surface.
Figure 4B:
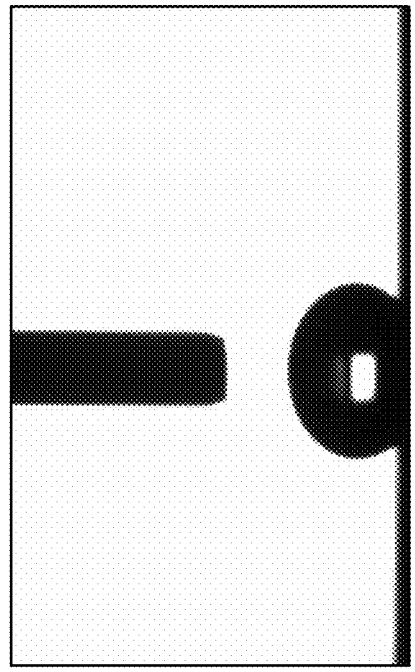
FIG. 4B is a photograph showing a water drop disposed on an etched dentin surface.
Figure 4C:
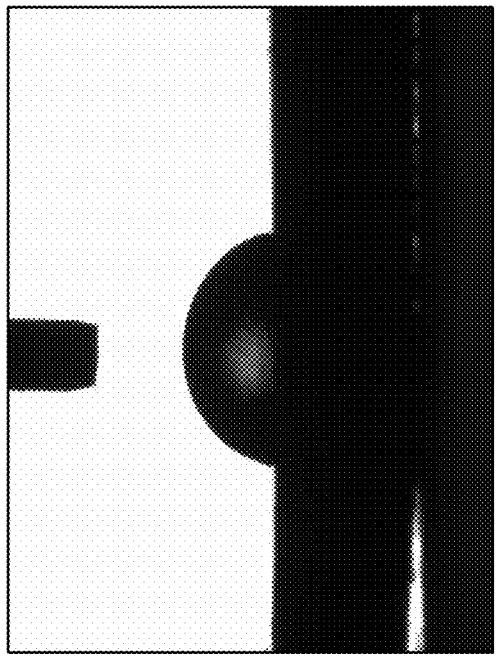
FIG. 4C is a photograph showing a water drop disposed on a dentin surface rinsed with alcohol after GL13K treatment.
Figure 4D:
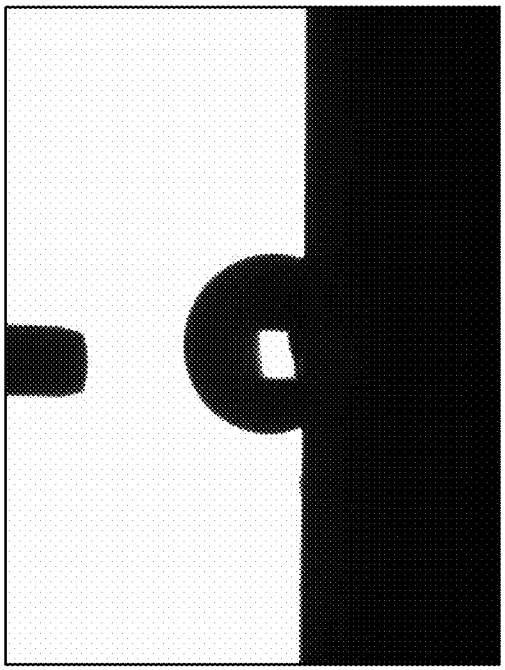
FIG. 4D is a photograph showing a water drop disposed on a dentin surface rinsed with solutions of increasing alcohol concentration after GL13K treatment.

The hypothesis was confirmed with the highest and most stable WCA among all GL13K-coated dentin tested, WCA=120° with ΔWCA=4°, on applying a progressive dehydration protocol, as shown in TABLE 1 (samples S1-S11) and FIG. 3. FIG. 3 is a chart presenting water contact angle as a function of time for untreated dental surfaces and dental surfaces treated with GL13K. FIG. 4A is a photograph showing a water drop disposed on an untreated dentin surface. FIG. 4B is a photograph showing a water drop disposed on an etched dentin surface. FIG. 4C is a photograph showing a water drop disposed on a dentin surface rinsed with alcohol after GL13K treatment. FIG. 4D is a photograph showing a water drop disposed on a dentin surface rinsed with solutions of increasing alcohol concentration after GL13K treatment.

To validate the use of other amphipathic peptides to obtain hydrophobic dentin, single or double coatings with 1018 and D-GL13K peptides on dentin were tested. Coated dentin with 1018 or D-GL13K peptides had WCA from 84° to 97° and WCA from 95° to 96°, respectively, as shown in TABLE 1 (samples S13-S16). WCA for all peptide coated dentin conditions were higher than dentin treated with the buffer solution without peptides, as shown in TABLE 1 (samples S17-S19). A quick method with a single coating of D-GL13K and simple rinsing with water produced a highly hydrophobic dentin with WCA=96° and ΔWCA=5° (sample S13).

A dentin preparation method with the aim of significantly increasing and homogenizing the mineral content at the prepared dentin surface before peptide coating was investigated (EXAMPLE 8). Dentin prepared with the deproteinized method and coated with GL13K, D-GL13K, or 1018 peptides had WCA=85°, 95° and 84°, respectively, as shown in TABLE 1 (samples S12, S14, and S16).

TABLE 1

| Sample No. | Treatment | Final Contact Angle (°) | Δ Contact Angle (°) |
| --- | --- | --- | --- |
| S1 | Etched Dentin | 20 | 25 |
| S2 | Single GL13K coat - water rinse | 70 | 15 |
| S3 | Single GL13K coat - alcohol rinse | 55 | 5 |
| S4 | Double GL13K coats - 2nd alcohol/enamel | 100 | 12 |
| S5 | Double GL13K coats - 1st alcohol/enamel | 90 | 10 |
| S6 | Double GL13K coats - 2nd alcohol/pulp | 90 | 6 |
| S7 | Double GL13K coats - 1st alcohol/pulp | 80 | 8 |
| S8 | Double GL13K coats - No alcohol/pulp | 70 | 17 |
| S9 | Alcohol before double GL13K coats/pulp | 80 | 12 |
| S10 | Double GL13K coats - Progressive alcohol rinse/pulp | 104 | 4.5 |
| S11 | Double GL13K coats - Progressive alcohol rinse/enamel | 120 | 4 |
| S12 | Deproteinization, double GL13K coats with water rinse/enamel-pulp | 85 | 10 |
| S13 | Single D-GL13K coat with water rinse/enamel-pulp | 96 | 5 |
| S14 | Deproteinization, single D-GL13K coat with water rinse/enamel-pulp | 95 | 5 |
| S15 | Double 1018 coats with progressive alcohol/enamel-pulp | 97 | 8 |
| S16 | Deproteinization, double 1018 coats/enamel-pulp | 84 | 12 |
| S17 | $Na_2CO_3$ coat - Water rinse | 45 | 20 |
| S18 | $Na_2CO_3$ coat - alcohol rinse | 45 | 5 |
| S19 | $Na_2CO_3$ coat - progressive alcohol rinse/pulp | 60 | 18 |

Example 2

Figure 5A:
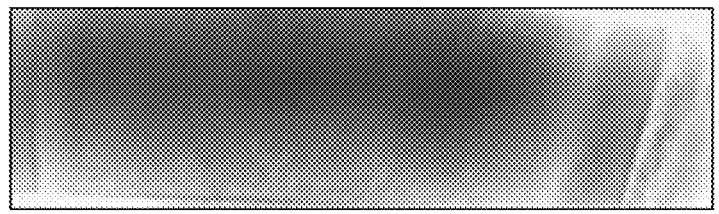
FIG. 5A is a photograph showing a facial view of a tooth slab including enamel and dentin and treated with a buffer solution, subjected to an acidic blue dye.
Figure 5B:
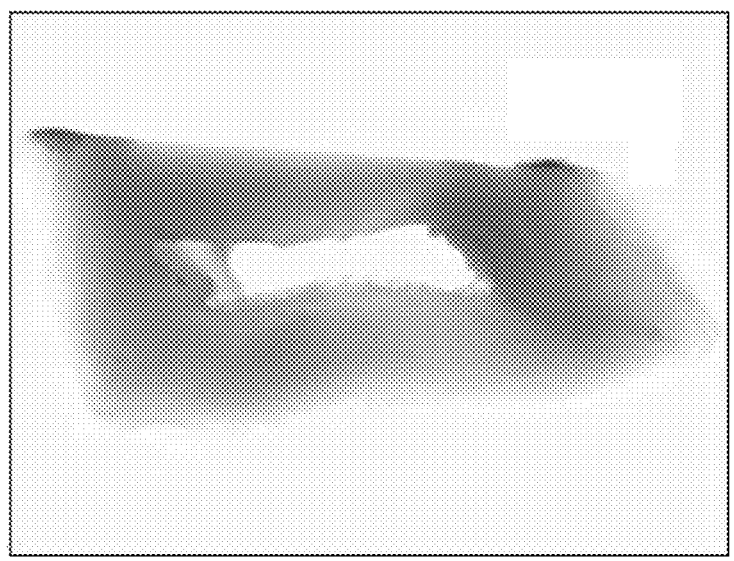
FIG. 5B is a photograph showing a transverse cross-section of a tooth slab including enamel and dentin and treated with a buffer solution, subjected to an acidic blue dye.
Figure 5C:
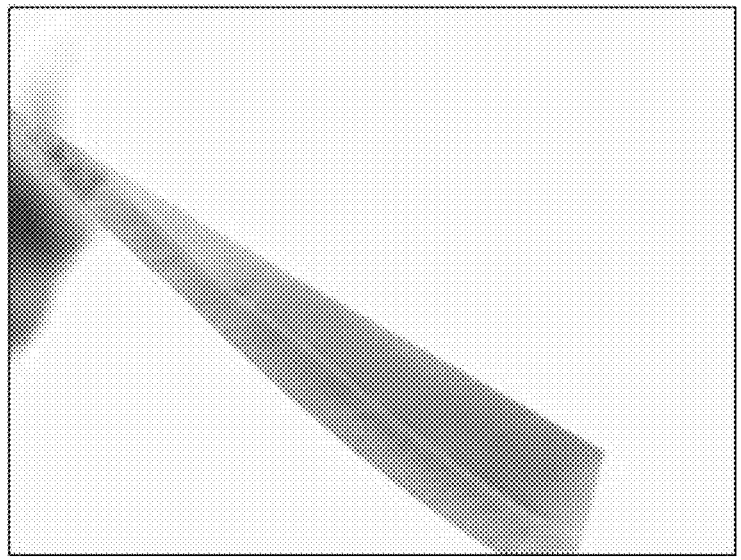
FIG. 5C is a photograph showing a longitudinal faciolingual section of a tooth slab including enamel and dentin and treated with a buffer solution, subjected to an acidic blue dye.
Figure 6A:
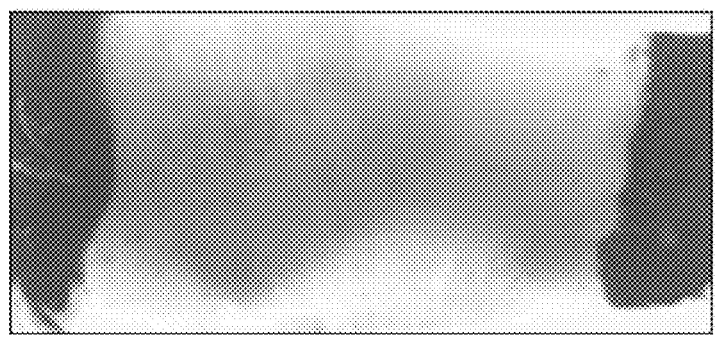
FIG. 6A is a photograph showing a facial view of a tooth slab including enamel and dentin and treated with GL13K, subjected to an acidic blue dye.
Figure 6B:
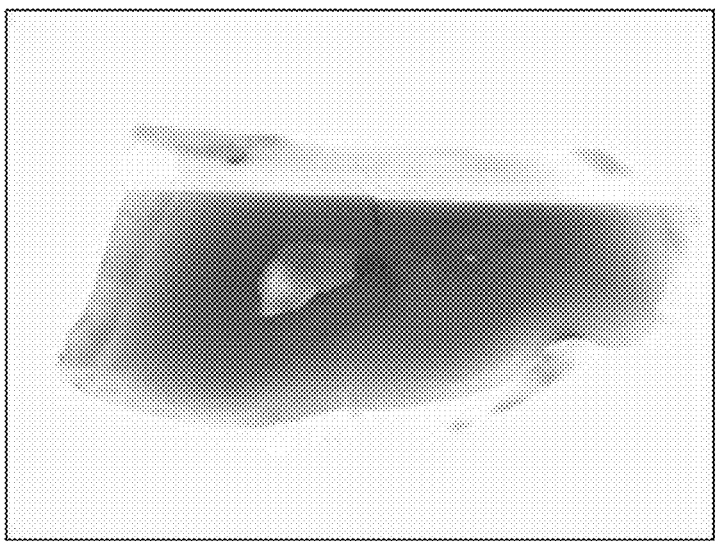
FIG. 6B is a photograph showing a transverse cross-section of a tooth slab including enamel and dentin and treated with GL13K, subjected to an acidic blue dye.
Figure 6C:
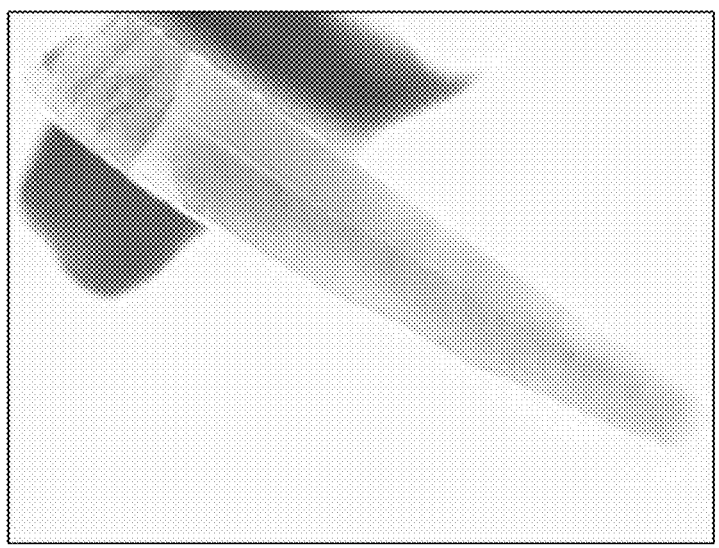
FIG. 6C is a photograph showing a longitudinal faciolingual section of a tooth slab including enamel and dentin and treated with GL13K, subjected to an acidic blue dye.

The ability of GL13K-coated dentin to resist penetration of biodegrading acidic water-borne agents was assessed, because dental caries progression is catalyzed by acidogenic bacteria that activate enzymes capable of degrading dentin. All surfaces of bovine dentin slabs were covered with two layers of nail varnish with the exception of a window that was coated with amphipathic GL13K peptides. The samples were immersed, along with control samples that did not have the coating, in a copper sulfate ($CuSO_4$) acidic blue dye solution with pH=3.4 for 4 hours. The penetration of the dye through the samples before and after sectioning the slabs either longitudinally (FIGS. 5A, 6A), transversely (FIGS. 5B, 6B), or facio-lingually (FIGS. 5C 6C) was evaluated. FIG. 5A is a photograph showing a facial view of a tooth slab including enamel and dentin and treated with a buffer solution, subjected to an acidic blue dye. FIG. 5B is a photograph showing a transverse cross-section of a tooth slab including enamel and dentin and treated with a buffer solution, subjected to an acidic blue dye. FIG. 5C is a photograph showing a longitudinal facio-lingual section of a tooth slab including enamel and dentin and treated with a buffer solution, subjected to an acidic blue dye. FIG. 6A is a photograph showing a facial view of a tooth slab including enamel and dentin and treated with GL13K, subjected to an acidic blue dye. FIG. 6B is a photograph showing a transverse cross-section of a tooth slab including enamel and dentin and treated with GL13K, subjected to an acidic blue dye. FIG. 6C is a photograph showing a longitudinal facio-lingual section of a tooth slab including enamel and dentin and treated with GL13K, subjected to an acidic blue dye. As seen in FIGS. 5A-6C, GL13K-coated dentin was hydrophobic and resisted acidic attack as the blue dye did not penetrate through its treated surface.

Example 3

Figure 7A:
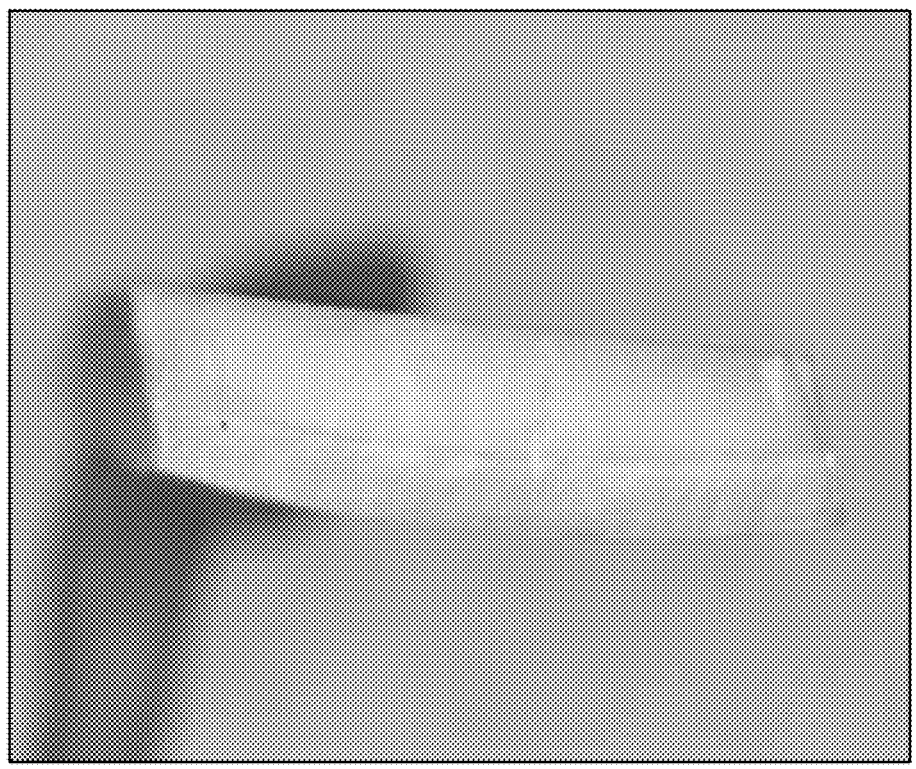
FIG. 7A is a photograph showing a transverse cross-section of a tooth slab including enamel and dentin and treated with a buffer solution, exposed to saliva for three days, and subjected to an acidic blue dye.
Figure 7B:
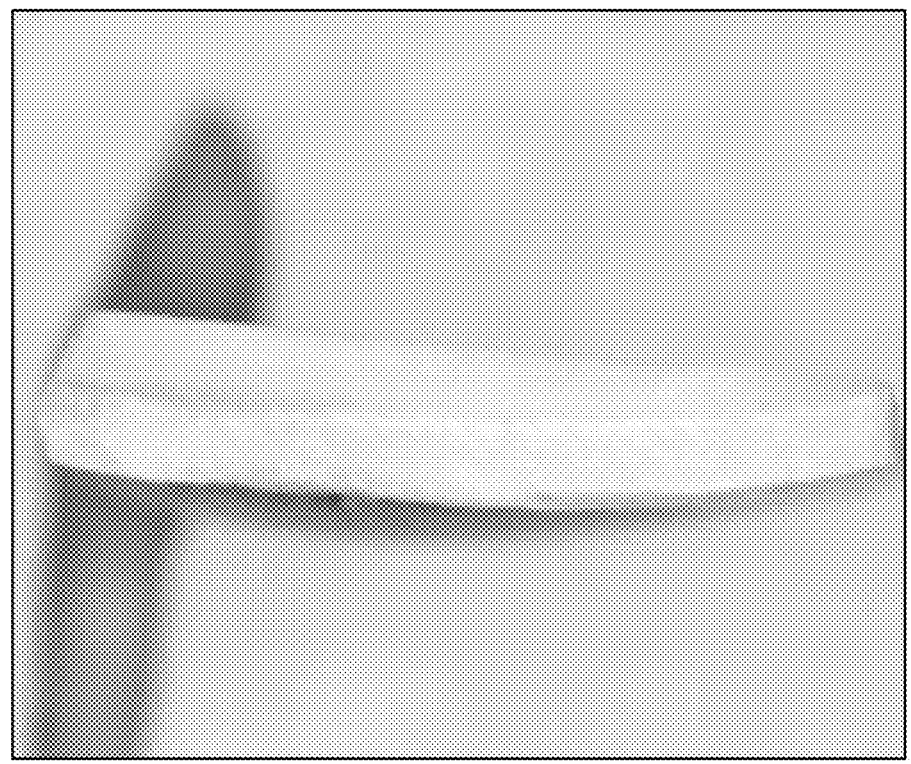
FIG. 7B is a photograph showing a transverse cross-section of a tooth slab including enamel and dentin and treated with GL13K, exposed to saliva for three days, and subjected to an acidic blue dye.

Peptide-coated dentin samples were challenged with saliva, which includes enzymes. Bovine dentin slabs, prepared as discussed above with reference to EXAMPLE 2, were incubated in freshly collected and filtered saliva (thus exposed to biodegrading enzymes) at 37° C. for three consecutive days. The WCA was subsequently measured, and the samples were further immersed in acidic blue dye for 4 h. GL13K-coated dentin retained its hydrophobic character after the challenge, with average WCA=105°. FIG. 7A is a photograph showing a transverse cross-section of a tooth slab including enamel and dentin and treated with a buffer solution, exposed to saliva for three days, and subjected to an acidic blue dye. FIG. 7B is a photograph showing a transverse cross-section of a tooth slab including enamel and dentin and treated with GL13K, exposed to saliva for three days, and subjected to an acidic blue dye. Acidic dye penetration was intense through the control non-coated dentin surfaces, whereas almost no dye penetration occurred in the hydrophobic dentin, as seen in FIGS. 5A and 5B. Thus an impervious hydrophobic dentin surface that resisted, at least short-term acidic and enzymatic degradation was demonstrated.

Example 4

Figure 8A:
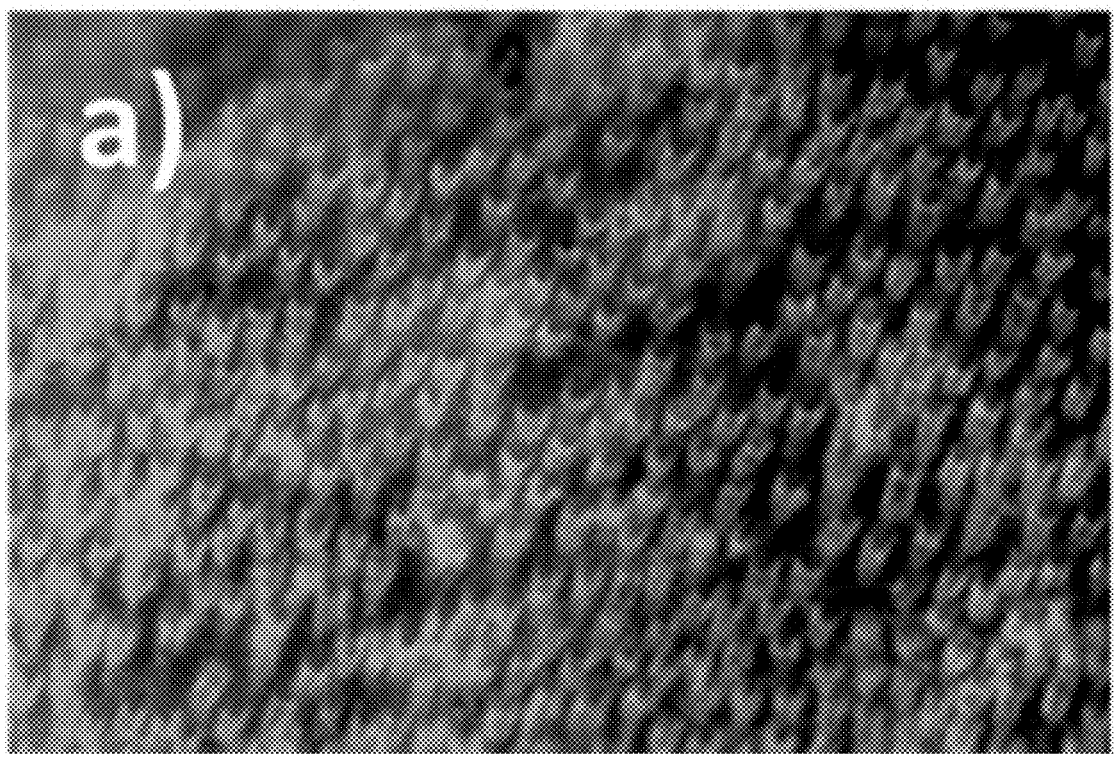
FIG. 8A is a photograph showing a fluorescence microscopy image of an etched dentin surface treated with fluorescently-labeled GL13K.
Figure 8B:
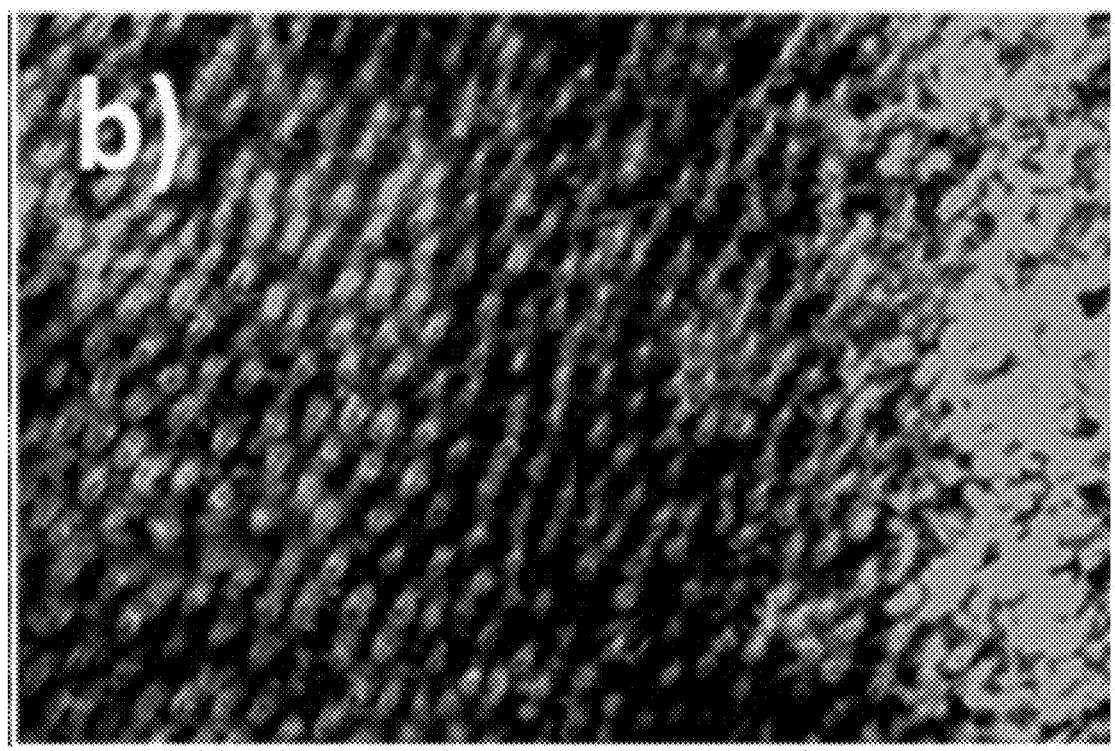
FIG. 8B is a photograph showing a fluorescence microscopy image of an etched dentin surface treated with fluorescently-labeled GL13K.

Dentin samples coated with fluorescently-labeled GL13K-peptides were imaged by fluorescence microscopy. Total-etched dentin samples were coating with labeled GL13K, using 5-FAM cadaverine fluorescence probe (green). FIG. 8A is a photograph showing a fluorescence microscopy image of an etched dentin surface treated with fluorescently-labeled GL13K, at 40× magnification. FIG. 8B is a photograph showing a fluorescence microscopy image of etched enamel treated with fluorescently-labeled GL13K, at 20× magnification, with enamel on the right edge and dentin on the left side. As seen in FIGS. 8A and 8B, GL13K was distributed over the surface of dentin, but was preferentially located on peritubular dentin (FIG. 8A). Peritubular dentin has significantly higher mineral content than intertubular dentin. Hydroxyapatite, the mineral phase of dentin, has a zero charge at pH=7.3. This may indicate that with the peptide solution at a basic pH, where the peptides are positively charged, there will be preferential electrostatic attraction between the mineral in dentin and the peptides. The strong electrostatic attraction between the positively charged GL13K peptides and the negatively charged etched dentin surface may be responsible for increasing its adsorption on the more mineralized structure rather than the organic collagenous one. That may also explain why enamel expressed the highest fluorescent signal, which is proportional with the mineral content (right edge of FIG. 8B).

Example 5

Figure 9:
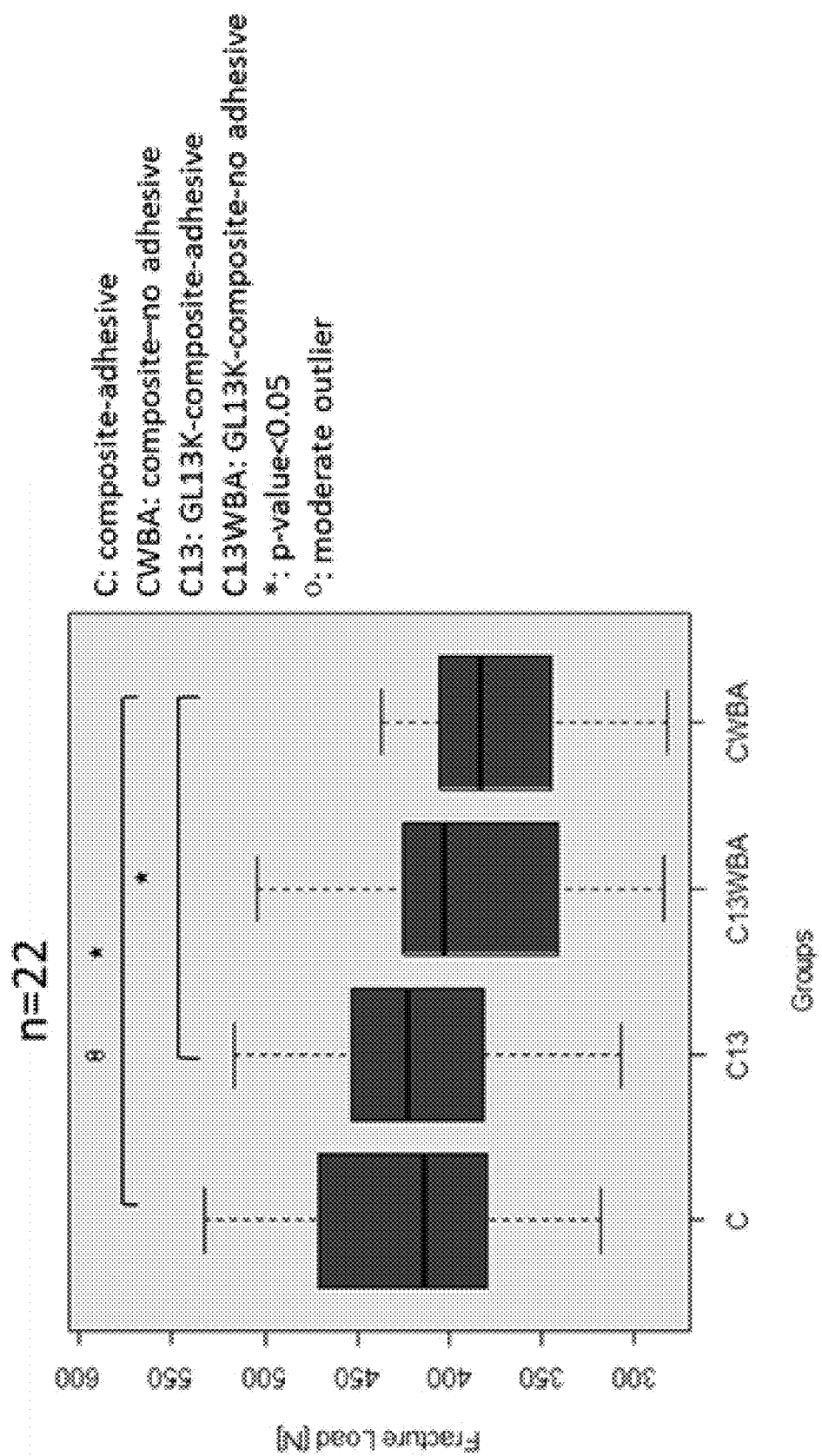
FIG. 9 is a chart comparing diametral-compression fracture loads of example dentin discs restored with dental resin composite, with and without using adhesive system, treated with GL13K to untreated discs.

The fracture resistance of restored dentin discs in diametral compression with GL13K coating was compared to discs without GL13K coating. Bovine roots used for preparing the sample discs were randomly divided into five groups according to the restorative treatment (22 discs each). All roots were total-etched as a first step of treatment. Scotch Bond Universal Adhesive (Ad) (3M, Saint Paul, Minn.) and Filtek Z250 composite (Cp) (3M, Saint Paul, Minn.) were used as the restorative materials. Progressive alcohol dehydration protocol was used with the GL13K coating. The five groups included: (1) group C: composite on non-GL13K-coated dentin, positive control (Ad+Cp); (2) group CWBA: composite without bonding agent in non-GL13K-coated dentin, negative control (Cp); (3) group C13: composite in GL13K-coated dentin (GL13K+Ad+Cp); (4) group C13WBA: composite without bonding agent in GL13K-coated dentin (GL13K+Cp); and (5) group C13CL: composite in GL13K-coated dentin, treated with NaOCl (sodium hypochlorite, for deproteinization). FIG. 9 is a chart comparing diametral-compression fracture loads of example dentin discs restored with dental resin composite, with and without using adhesive system, treated with GL13K to untreated discs, showing results for the first four groups. Most sample discs deformed linearly with increasing load until fracture occurred. As seen in FIG. 9, the presence of the super hydrophobic layer of GL13K at the dentin surface did not lower the bond strength of the dentin-restoration interface. The highest resistance to failure was achieved in the group C13, even though the bonding agent used was notably hydrophilic. In the groups without GL13K, removal of the bonding agent significantly lowered the mechanical strength. In contrast, this reduction was not statistically significant in specimens with hydrophobic dentin. Thus, when the components of the restorative system were modified with increased hydrophobicity, improved bond strength of the restoration may be achieved.

Example 6

Figure 10A:
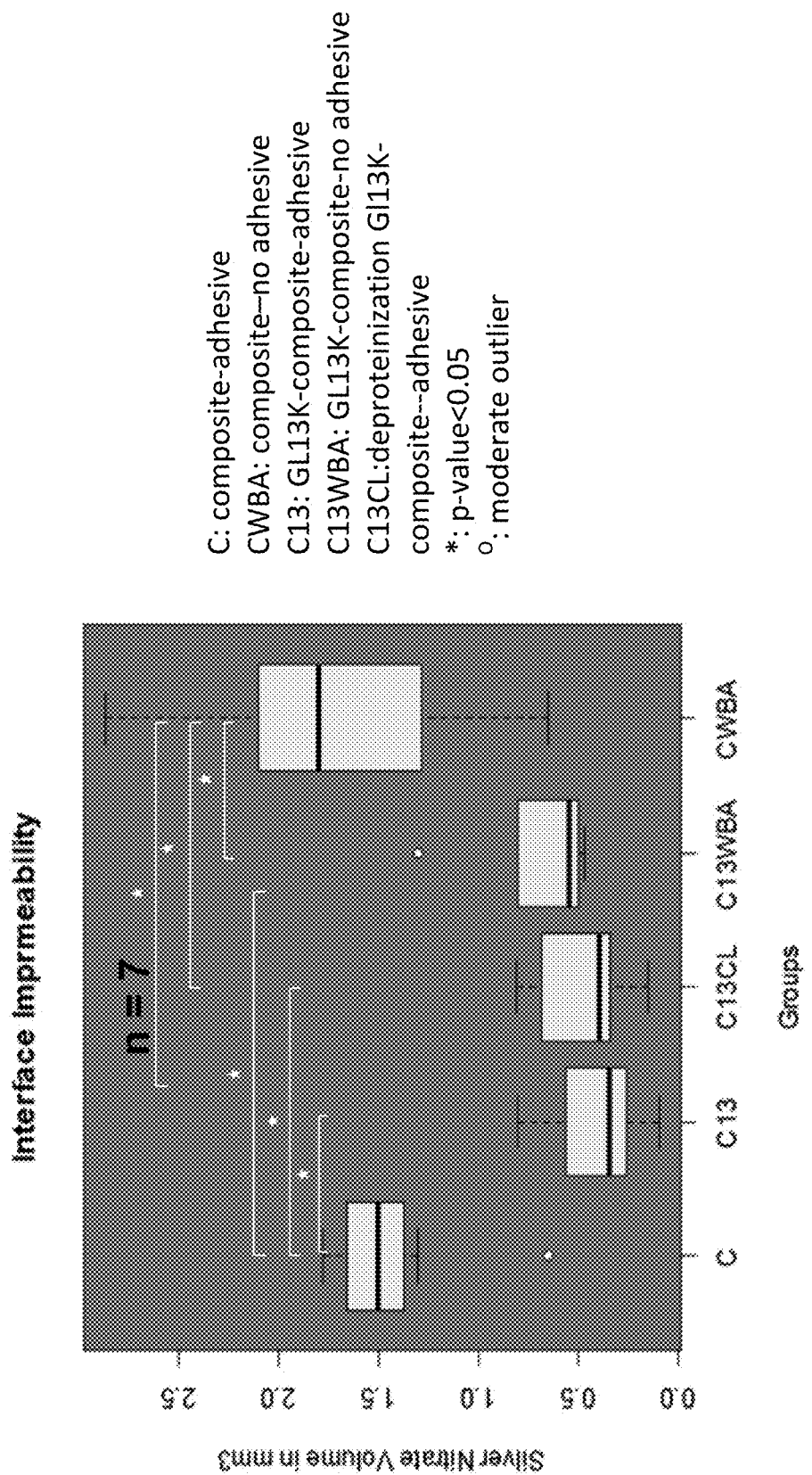
FIG. 10A is a chart comparing interfacial water impermeability of example dentin discs restored with dental resin composite, with and without using adhesive systems, treated with GL13K to untreated discs, before aging.

The interface impermeability of the discs of the five groups of EXAMPLE 5 was evaluated. Micro-computed tomography (μ-CT) was used to image cross-sections of sample discs without destroying the discs. Radioopaque dye (silver nitrate, $AgNO_3$) was used to assess leakage at the dental surface/restoration interfaces. The μ-CT images were used to estimate silver nitrate volume penetrated into the sample discs. FIG. 10A is a chart comparing interfacial water impermeability of example dentin discs restored with dental resin composite, with and without using adhesive systems, treated with GL13K to untreated discs, prior to aging. As seen in FIG. 10A, composite-dentin interfaces of discs treated with GL13K exhibited significantly lower permeability than untreated discs, regardless of whether bonding agents were applied to the interface or not.

Example 7

Figure 10B:
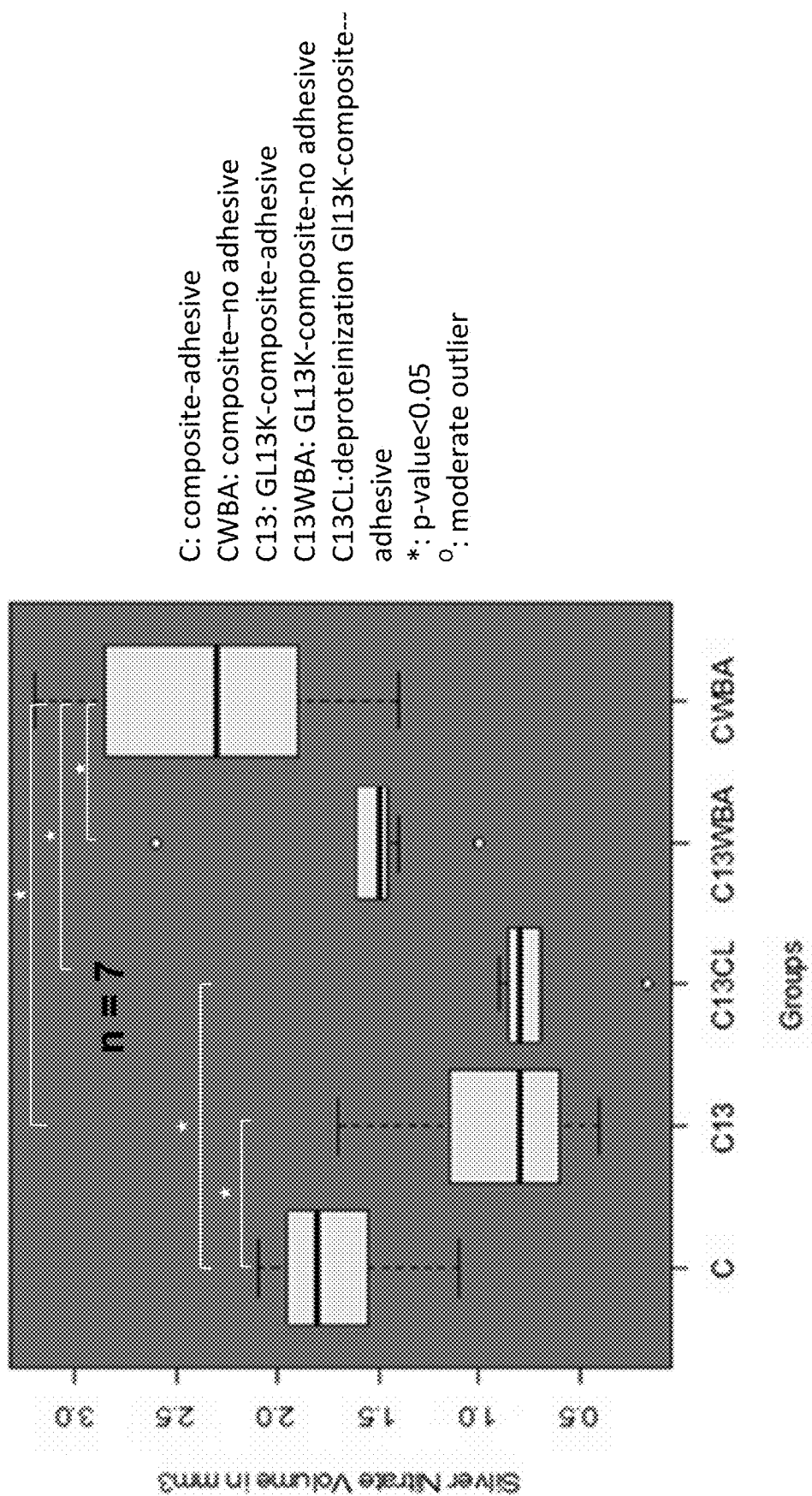
FIG. 10B is a chart comparing interfacial water impermeability of example dentin discs restored with dental resin composite, with and without using adhesive systems, treated with GL13K to untreated discs, after aging.

The effect of aging on the discs of the five groups of EXAMPLES 5 and 6 was investigated. Aging consisted of 2-month storage in water followed by 2,500 thermal cycles (5° C. to 55° C., 30 s each with 5 s transfer time), which approximately corresponds to 3 months of clinical function. FIG. 10B is a chart comparing interfacial water impermeability of example dentin discs restored with dental resin composite, with and without using adhesive systems, treated with GL13K to untreated discs, after aging. As seen by comparing FIGS. 10A and 10B, the GL13K hydrophobic peptide coatings had significantly reduced silver nitrate penetration right after restoring the samples in comparison to the control samples, and the reduction was also significant after the aging protocol. This was also true for samples where no bonding agent was applied. In addition, no significant increase in silver nitrate volume penetration was detected after aging for samples with super-hydrophobic GL13K-coated dentin that were restored using bonding agent. Thus, the peptide coatings do not significantly degrade and, thus, maintain their main active property over extended periods of simulated oral conditions.

Example 8

A dentin preparation method with the aim of significantly increasing and homogenizing the mineral content at the prepared dentin surface before peptide coating was investigated. A de-proteinization step was used to remove demineralized/exposed collagen. The process of this example included (1) etching dentin, (2) wet de-proteinization of exposed collagen with 5% NaOCl solution, and (3) GL13K peptide coating without alcohol dehydration. A super-hydrophobic GL13K-coated dentin surface with water contact angles up to 100 was produced.

Example 9

The antimicrobial potency of etched and D-GL13K coated hydroxyapatite (HA) discs was compared to etched discs without D-GL13K coating. Etched HA discs were used to simulate mineral phase of dentin, with similar chemical characteristics than surfaces obtain in example 8. 5 ml of the modified BHI medium was inoculated with microcosm multispecies biofilm derived from caries active subjects. After overnight anaerobic incubation, the optical density ($OD_{600}$), was adjusted at 0.2±0.01 followed by 1:10, corresponding to 5.0×106 CFU/ml. 12 samples per each group; i.e., peptide coated and non-coated discs were tested. After sterilizing HA discs by autoclaving, the discs were etched by 35% phosphoric acid gel for 15 sec followed by 10 sec rinse and air dry for 10 sec. For the D-GL13K coated discs, double coatings were applied at a concentration followed by air-drying for 60 seconds. Each disc was inoculated with 200 of the adjusted inoculum and then 1.8 ml of fresh media was added. The plate was incubated for 48 hours at 37° in the anaerobic chamber with mild shaking. Each disc was washed with PBS with care to remove the unattached bacteria. The discs were stained with 0.1% Crystal Violet (CV) solution for 15 mins at room temp. The excess CV satin was washed off with distilled water followed by imaging for qualitative assessment.

Figure 11A:
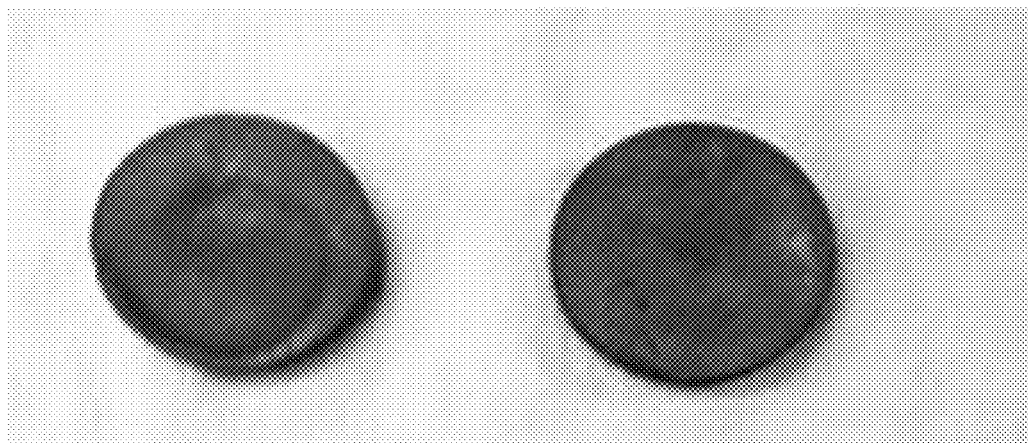
FIG. 11A is a photograph showing images of crystal violet stained multispecies bacterial biofilm on uncoated hydroxyapatite discs.
Figure 11B:
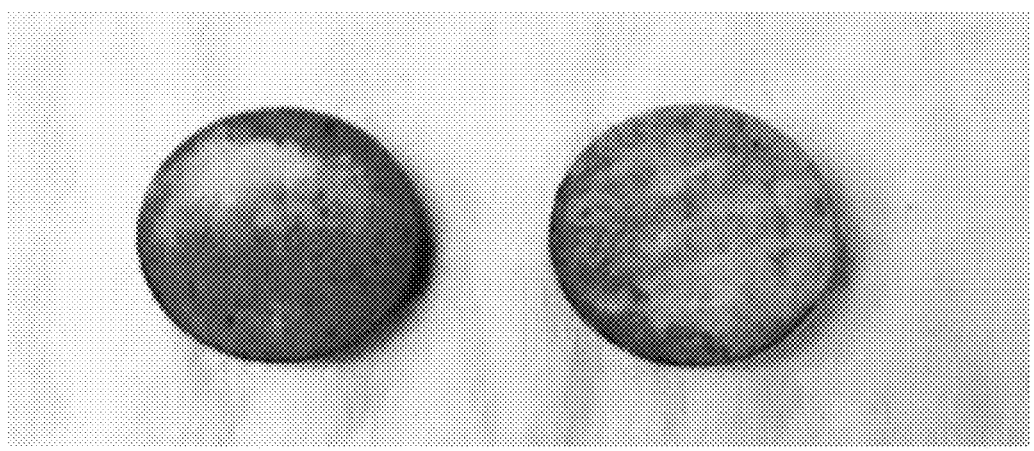
FIG. 11B is a photograph showing images of crystal violet stained multispecies bacterial biofilm on D-GL13K coated hydroxyapatite discs.
Figure 11C:
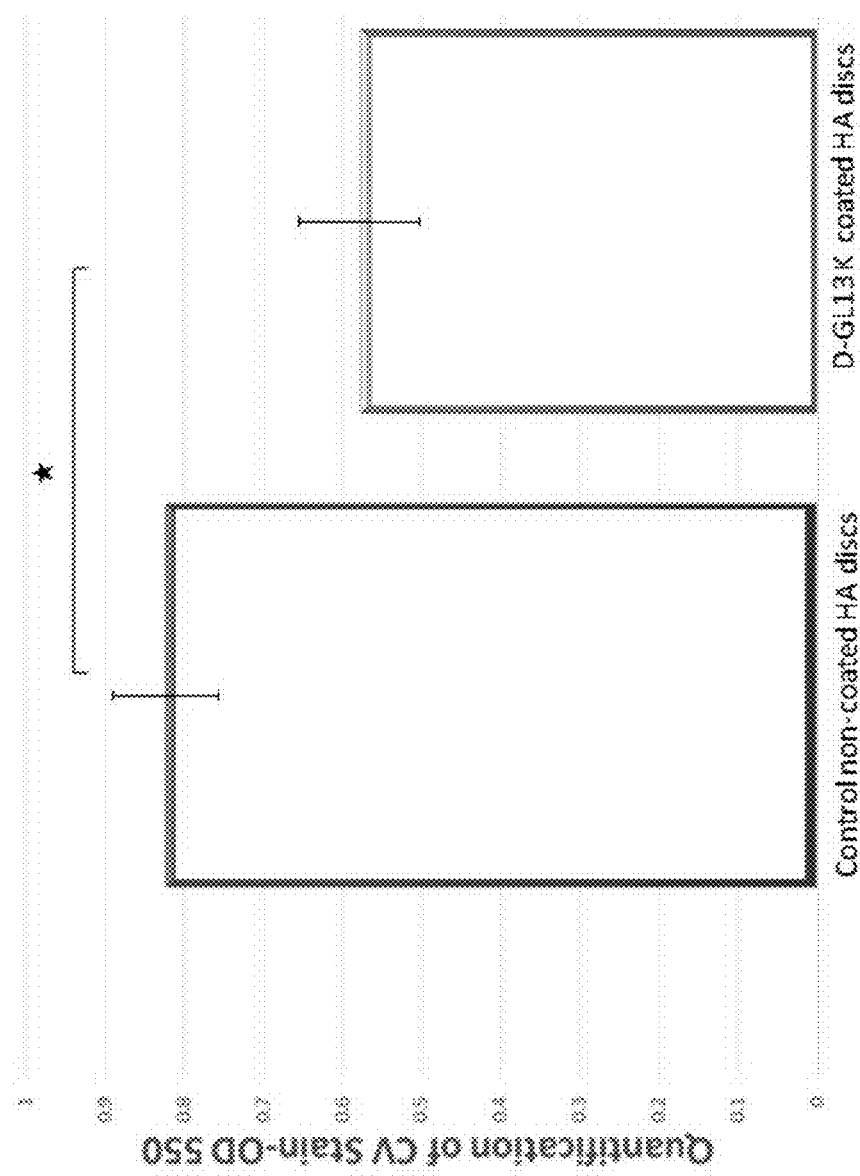
FIG. 11C is a chart comparing bioburden growth from multispecies bacteria biofilm on D-GL13K coated hydroxyapatite discs and uncoated discs.

FIG. 11A is a photograph showing images of crystal violet stained multispecies bacterial biofilm on uncoated hydroxyapatite discs. FIG. 11B is a photograph showing images of crystal violet stained multispecies bacterial biofilm on D-GL13K coated hydroxyapatite discs. FIG. 11C is a chart comparing bioburden growth from multispecies bacteria biofilm on D-GL13K coated hydroxyapatite discs and uncoated discs. Notable reduction of multispecies biofilm on the D-GL13K coated surfaces was observed in comparison to non-coated HA discs. To quantify the biofilm grown on the discs, the stain was solubilized in 30% acetic acid and measured at $OD_{550}$. The amount of biofilm was significant reduced (two-sample t-test; p-value=0.014) on D-GL13K coated HA discs in comparison to non-coated HA discs, as shown in FIG. 11A.

To quantify the number of bacteria grown on D-GL13K coated and non-coated HA discs, the discs were washed with 0.9% NaCl to remove the unattached bacteria. To remove the attached bacteria on the surfaces of the disks, biofilms were treated with a magnetostrictive ultrasonic scaler at medium power setting without cooling water irrigation. Ultrasonication was conducted for 90 seconds under cold (4° C.) 0.9% NaCl immersion. The whole process was conducted on ice to compensate for the high temperature generated from sonication and thus, to maintain vitality of the removed bacteria. Serial dilution was done up to $10^8$. Then, colony forming units (CFU) were measured.

Figure 12:
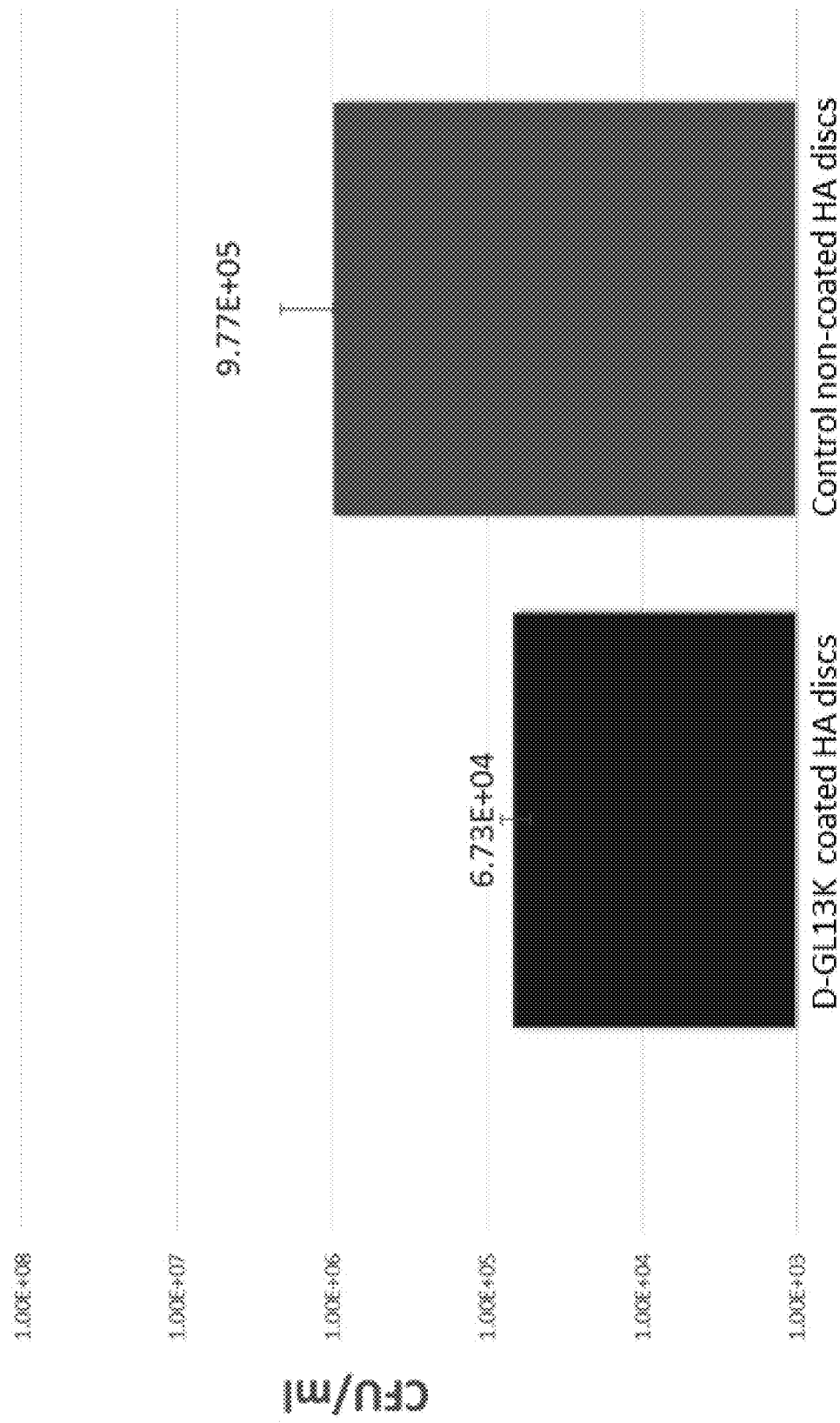
FIG. 12 is a chart comparing colony forming units (CFU) of multispecies bacteria biofilm grown and recovered from D-GL13K coated hydroxyapatite discs and non-coated discs.

FIG. 12 is a chart comparing colony forming units (CFU) of multispecies bacteria biofilm grown and recovered from D-GL13K coated hydroxyapatite discs and non-coated discs. CFU values of the recovered multispecies biofilms from non-coated HA discs were more than one fold higher than from D-GL13K coated discs, as shown in FIG. 12. This is a notable antibiofilm effect of the of the hydrophobic and antimicrobial peptide coatings.

Example 10

To evaluate the bactericidal effect of D-GL13K coated hydroxyapatite (HA) discs multispecies bacteria biofilms were grown as described in EXAMPLE 9 on D-GL13K coated and non-coated HA disks and a fluorescent Live/Dead bacteria vitality assay on the grown biofilms was performed. Working solutions of fluorescent stains was prepared by adding 3 μL of SYTO® 9 stain (ThermoFisher Scientific, Waltham, Mass.) and 3 μl of propidium iodide stain to 1 ml of filter-sterilized water. The discs were submerged into 0.9% NaCl very gently to remove the unattached bacteria. 100 μl of staining solution was added onto the biofilm sample very gently so as not to disturb the biofilm. After 20-30 minutes light protected incubation at room temperature, the discs were examined using an upright fluorescence microscope using a 40× water immersion lens.

Figure 13A:
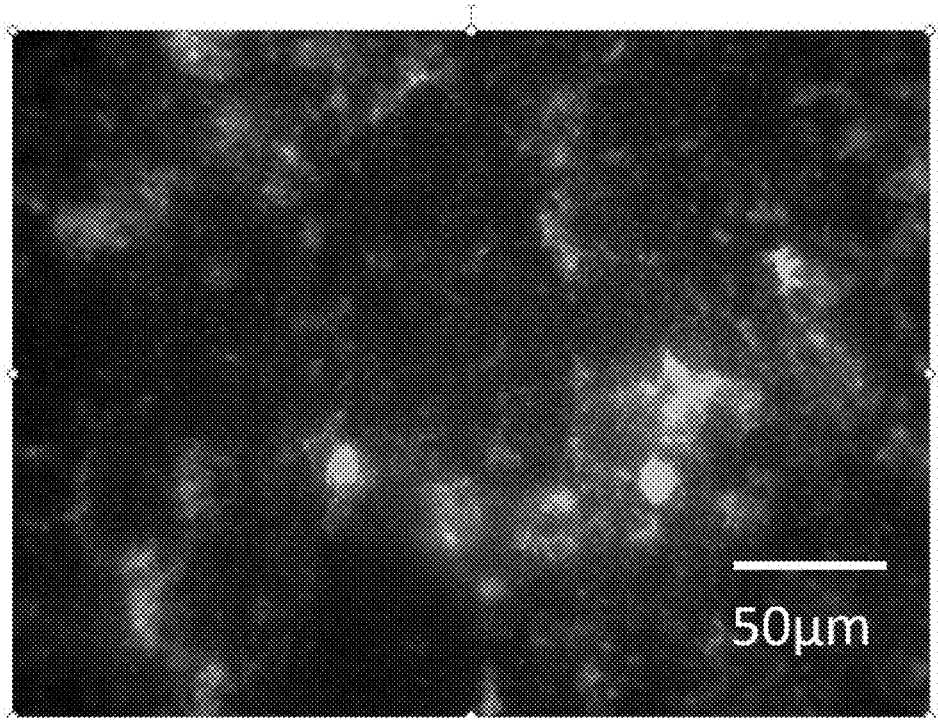
FIG. 13A is a fluorescent image of bacteria biofilm grown on a non-coated hydroxyapatite disc and stained with a Live/Dead cell vitality assay. Live bacteria stain green and dead bacteria stain red.
Figure 13B:
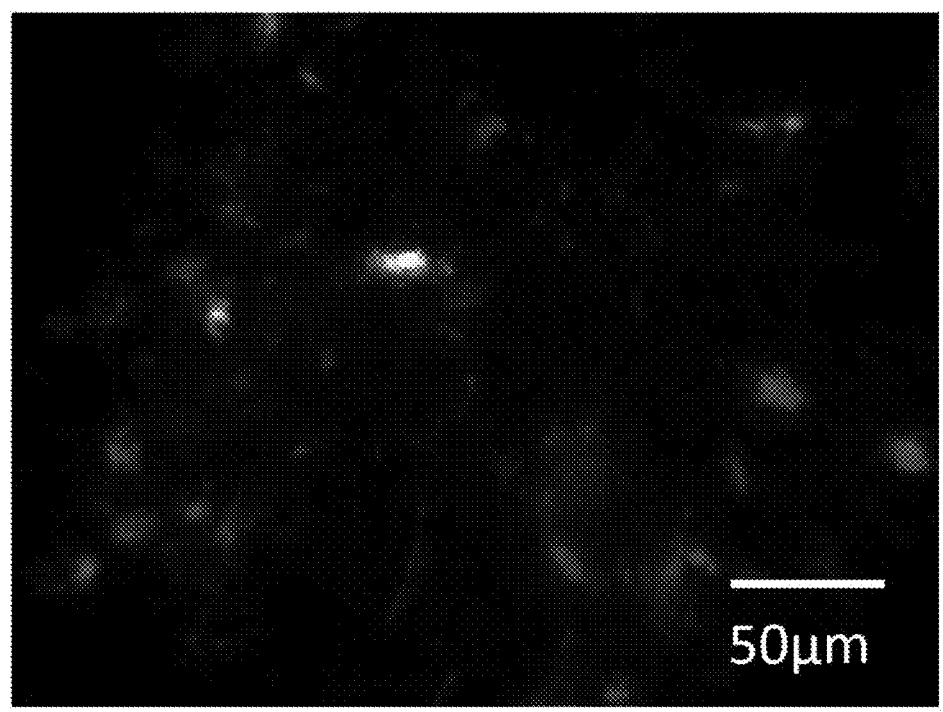
FIG. 13B is a fluorescent image of bacteria biofilm grown on a D-GL13K coated disc stained with a Live/Dead cell vitality assay. Live bacteria stain green and dead bacteria stain red.

FIG. 13A is a fluorescent image of bacteria biofilm grown on a non-coated hydroxyapatite disc and stained with a Live/Dead cell vitality assay. FIG. 13B is a fluorescent image of bacteria biofilm grown on a D-GL13K coated disc stained with a Live/Dead cell vitality assay. Live bacteria stain green (brighter) and dead bacteria stain red. The fluorescent images showed that most of biofilm bacteria on control non-coated HA discs were alive; i.e. stained green, as shown in FIG. 13A. However, most of biofilm bacteria were dead; i.e, stained red on the D-GL13K coated HA discs, as shown in FIG. 13B. Thus, D-GL13K hydrophobic and antimicrobial coatings were bactericidal.

Example 11

To evaluate the resistance to mechanical and chemical degradation of D-GL13K coatings on hydroxyapatite discs and their sustain bactericidal activity, D-GL13K coated and non-coated HA discs were ultrasonicated in distilled water for 45 mins and then multispecies biofilms were regrown for 5 more days as described in EXAMPLE 9. Bactericidal effects were tested with a LIVE/DEAD bacteria vitality assay following the protocol described in EXAMPLE 10.

Figure 14A:
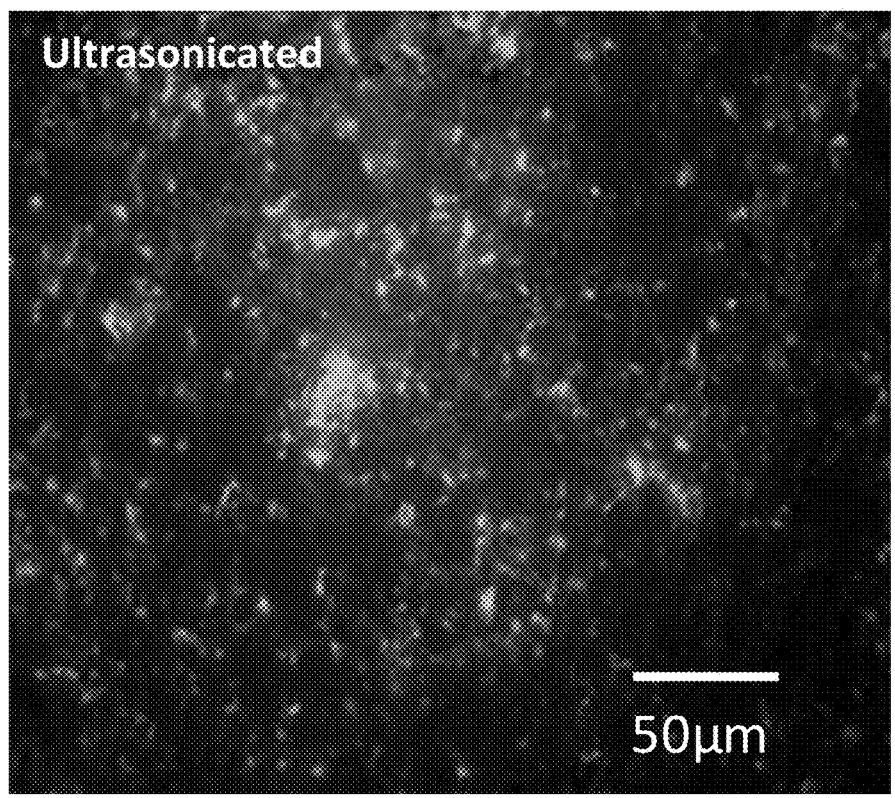
FIG. 14A is a photograph showing a fluorescent image of bacteria biofilm grown on a non-coated hydroxyapatite disc ultrasonicated in water for 45 mins.
Figure 14B:
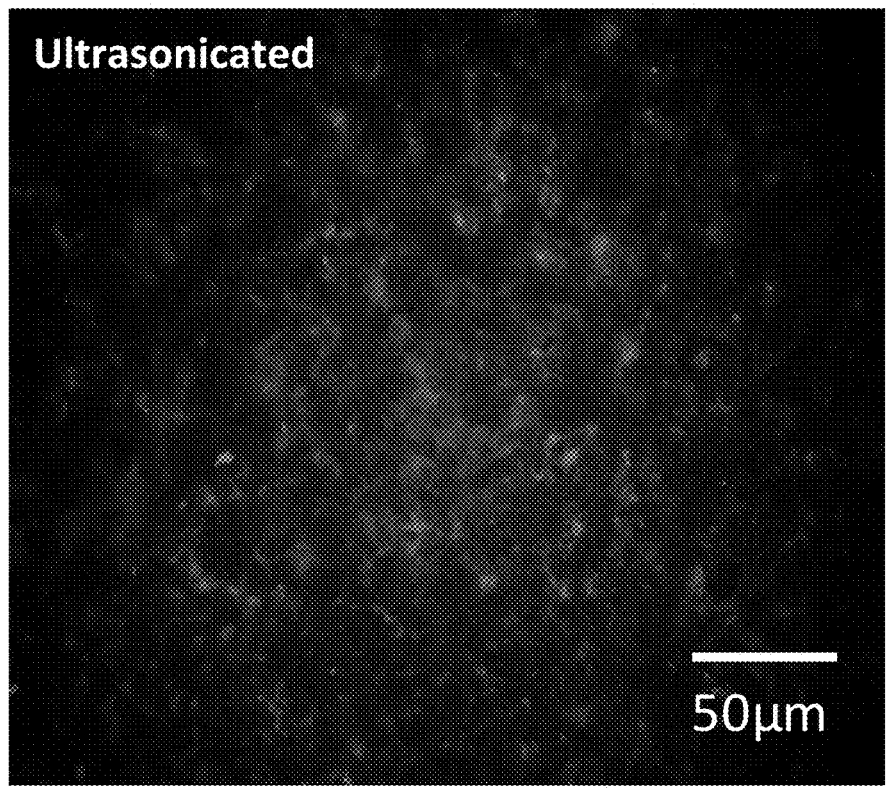
FIG. 14B is a photograph fluorescent image of bacteria biofilm grown on a D-GL13K coated hydroxyapatite disc ultrasonicated in water for 45 mins.
Figure 14C:
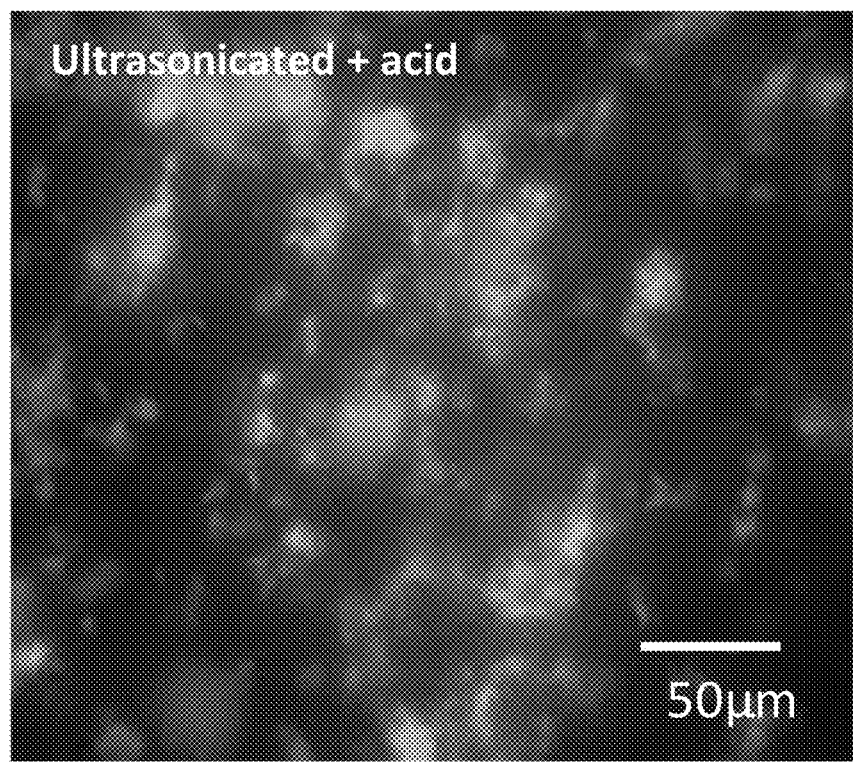
FIG. 14C is a fluorescent image of bacteria biofilm grown on a non-coated hydroxyapatite disc ultrasonicated in water for 45 mins and immersed in acid solution for 45 mins.
Figure 14D:
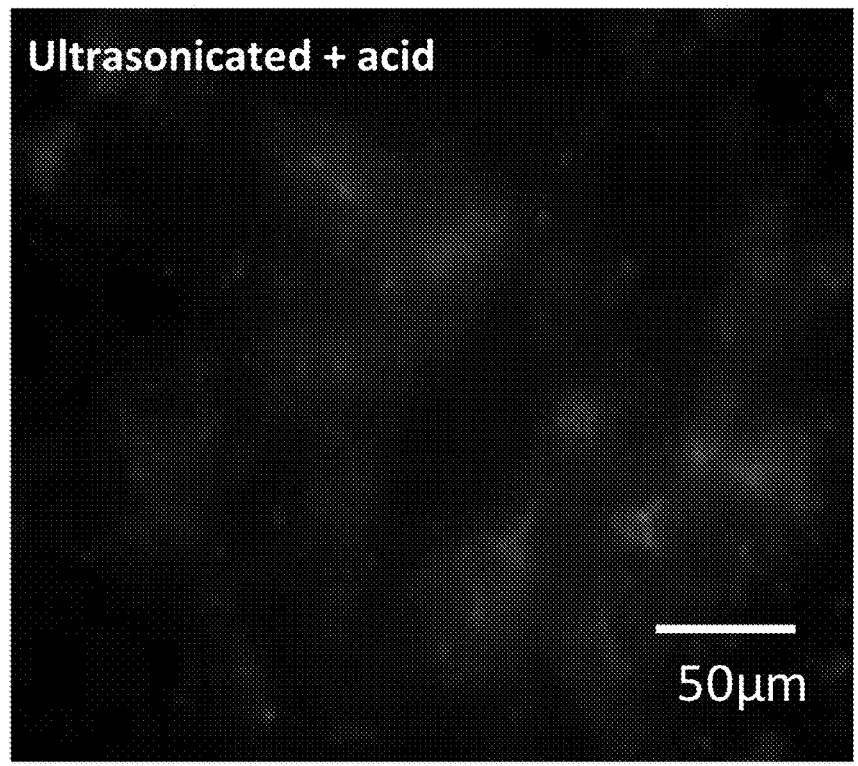
FIG. 14D is a fluorescent image of bacteria biofilm grown on a D-GL13K coated hydroxyapatite disc ultrasonicated in water for 45 mins and immersed in acid solution for 45 mins.

FIG. 14A is a photograph showing a fluorescent image of bacteria biofilm grown on a non-coated hydroxyapatite disc ultrasonicated in water for 45 mins. FIG. 14B is a photograph fluorescent image of bacteria biofilm grown on a D-GL13K coated hydroxyapatite disc ultrasonicated in water for 45 mins. FIG. 14C is a fluorescent image of bacteria biofilm grown on a non-coated hydroxyapatite disc ultrasonicated in water for 45 mins and immersed in acid solution for 45 mins. FIG. 14D is a fluorescent image of bacteria biofilm grown on a D-GL13K coated hydroxyapatite disc ultrasonicated in water for 45 mins and immersed in acid solution for 45 mins. The fluorescent images showed that most of biofilm bacteria on control non-coated HA discs were alive; i.e. stained green, as shown in FIG. 14A. However, most of biofilm bacteria were dead; i.e, stained red on the D-GL13K coated HA discs, as shown in FIG. 14B. Thus, D-GL13K hydrophobic and antimicrobial coatings were non degraded by the mechanical challenge and sustained their bactericidal activity.

Chemical challenge on the D-GL13K coated and non-coated HA discs was conducted after ultrasonication in water for 45 mins by immersion in 30% acetic acid, pH=2, for 45 mins and then the biofilms were regrown for 15 more days as described in EXAMPLE 9. Bactericidal effects were tested with a LIVE/DEAD bacteria vitality assay following the protocol described in EXAMPLE 10. The fluorescent images showed that most of biofilm bacteria on control non-coated HA discs were alive; i.e. stained green, as shown in FIG. 14C. However, most of biofilm bacteria were dead; i.e, stained red on the D-GL13K coated HA discs, as shown in FIG. 14D. Thus, D-GL13K hydrophobic and antimicrobial coatings were non degraded by the chemical challenge and sustained their bactericidal activity.

Various examples have been described. These and other examples are within the scope of the following claims.

What is claimed is:

1. A method comprising:
   applying an etchant composition on a dental surface to etch the dental surface;
   after applying the etchant composition, applying a coating composition comprising GL13K peptide to the dental surface to provide a hydrophobic coating on the dental surface, wherein the hydrophobic coating has a water contact angle of greater than or equal to about 50°; and
   applying a restorative layer to the hydrophobic coating, wherein the restorative layer comprises a hydrophobic resin composite.

2. The method of claim 1, further comprising, before applying the hydrophobic coating, applying a deproteinization agent to deproteinize the dental surface.

3. The method of claim 2, wherein the deproteinization agent comprises one or more of bleach, sodium hypochlorite, or proteolytic enzymes.

4. The method of claim 1, further comprising one or more of cutting the dental surface to expose a cavity, applying a deproteinization agent on the dental surface, applying a primer layer on the dental surface, and applying an adhesive layer on the dental surface.

5. The method of claim 1, wherein the dental surface comprises one or more of dentin, enamel, and a dental prosthetic.

6. The method of claim 1, wherein the water contact angle is greater than or equal to about 100°.

7. The method of claim 1, wherein the water contact angle is greater than or equal to about 120°.

8. The method of claim 1, wherein the coating composition consists of GL13K peptide and one or both of water and a buffer solution.

9. The method of claim 1, wherein the amphiphilic agent is an antimicrobial agent.

10. An article comprising:
    a hydrophobic coating layer comprising GL13K peptide; and
    a restorative layer, on the hydrophobic coating layer, wherein the restorative layer comprises a hydrophobic composite dental resin.

11. The article of claim 10, further comprising a primer layer adjacent the hydrophobic coating layer.

12. The article of claim 10, further comprising an adhesive layer adjacent the hydrophobic coating layer.

13. The article of claim 10, wherein the hydrophobic coating layer further comprises one or both of water and a buffer solution.

14. The article of claim 10, wherein the hydrophobic coating layer consists of GL13K peptide.

15. The article of claim 10, wherein the hydrophobic composite dental resin is curable by UV light.

16. A kit comprising:
    a kit body comprising one or more containers, wherein each container comprises a chamber configured to hold one or more compositions;
    a dental restorative composition, wherein the dental restorative composition comprises a hydrophobic resin composite; and
    a coating composition comprising GL13K peptide, wherein the coating composition is configured to be applied to a dental surface, and wherein the coating composition is configured to provide on the dental surface a hydrophobic coating with a water contact angle of greater than or equal to about 50°, wherein the dental restorative composition and the coating composition are held in separate chambers of one or more of the containers.

17. The kit of claim 16, further comprising one or more of a primer composition, an adhesive composition, an etchant composition, a dehydrating composition, and a deproteinization agent.

18. The kit of claim 16, wherein the coating composition is configured to provide a hydrophobic coating on the dental surface with a water contact angle greater than or equal to about 100°.

19. The kit of claim 16, wherein the coating composition is configured to provide a hydrophobic coating on the dental surface with a water contact angle greater than or equal to about 120°.

20. The kit of claim 16, wherein the coating composition consists of GL13K peptide and one or both of water and a buffer solution.

21. The kit of claim 16, wherein the coating composition consists of GL13K peptide.

22. The kit of claim 16, wherein the amphiphilic agent is an antimicrobial agent.

\* \* \* \* \*

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial
<220> FEATURE:
<223> OTHER INFORMATION: Synthetic peptide GL13K

<400> SEQUENCE: 1

Gly Lys Ile Ile Lys Leu Lys Ala Ser Leu Lys Leu Leu
1               5                   10

<210> SEQ ID NO 2
<211> LENGTH: 12
<212> TYPE: PRT
<213> ORGANISM: Artificial
<220> FEATURE:
<223> OTHER INFORMATION: Synthetic peptide 1018

<400> SEQUENCE: 2

Val Arg Leu Ile Val Ala Val Arg Ile Trp Arg Arg
1               5                   10
```